US011576887B2

(12) United States Patent
DAmore et al.

(10) Patent No.: US 11,576,887 B2
(45) Date of Patent: Feb. 14, 2023

(54) NITRO-OLEIC ACID CONTROLLED RELEASE PLATFORM TO INDUCE REGIONAL ANGIOGENESIS IN ABDOMINAL WALL REPAIR

(71) Applicant: University of Pittsburgh—Of the Commonwealth System of Higher Education, Pittsburgh, PA (US)

(72) Inventors: Antonio DAmore, Pittsburgh, PA (US); Marco Fazzari, Pittsburgh, PA (US); Bruce A. Freeman, Pittsburgh, PA (US); William R. Wagner, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/765,447

(22) PCT Filed: Nov. 19, 2018

(86) PCT No.: PCT/US2018/061862
§ 371 (c)(1),
(2) Date: May 19, 2020

(87) PCT Pub. No.: WO2019/100021
PCT Pub. Date: May 23, 2019

(65) Prior Publication Data
US 2020/0276144 A1 Sep. 3, 2020

Related U.S. Application Data

(60) Provisional application No. 62/588,830, filed on Nov. 20, 2017.

(51) Int. Cl.
| | | |
|---|---|---|
| *A61L 27/44* | (2006.01) | |
| *A61L 27/52* | (2006.01) | |
| *A61K 31/201* | (2006.01) | |
| *A61K 31/765* | (2006.01) | |
| *A61L 27/54* | (2006.01) | |
| *A61K 9/16* | (2006.01) | |
| *A61K 9/50* | (2006.01) | |

(52) U.S. Cl.
CPC .......... *A61K 31/201* (2013.01); *A61K 9/1647* (2013.01); *A61K 9/5031* (2013.01); *A61K 31/765* (2013.01); *A61L 27/44* (2013.01); *A61L 27/52* (2013.01); *A61L 27/54* (2013.01); *A61L 2300/114* (2013.01); *A61L 2300/622* (2013.01)

(58) Field of Classification Search
CPC .............. A61K 31/201; A61K 9/1647; A61K 9/5031; A61K 31/765; A61L 27/44; A61L 27/52; A61L 27/54; A61L 2300/114; A61L 2300/622
See application file for complete search history.

(56) References Cited

U.S. PATENT DOCUMENTS

| | | | |
|---|---|---|---|
| 7,776,916 B2 | 8/2010 | Freeman et al. | |
| 9,750,725 B2 | 9/2017 | Freeman et al. | |
| 2012/0213708 A1* | 8/2012 | Anderson | |
| 2013/0253663 A1* | 9/2013 | Amoroso | |

FOREIGN PATENT DOCUMENTS

| | | |
|---|---|---|
| WO | WO 2011/113507 | 9/2011 |
| WO | WO 2012/024390 | 2/2012 |
| WO | WO 2016/138423 | 9/2016 |

OTHER PUBLICATIONS

Oriakhi (Chemistry in Quantitative Language: Fundamentals of General Chemistry Calculations, Second Edition, 1 page, 2021) (Year: 2021).*
D'Amore et al. "Bi-layered polyurethane—Extracellular matrix cardiac patch improves ischemic ventricular wall remodeling in a rat model," *Biomaterials*, vol. 107, pp. 1-14, Nov. 2016.
Hong et al., "Tailoring the degradation kinetics of poly(ester-carbonate urethane) urea thermoplastic elastomers for tissue engineering scaffolds," *Biomaterials*, 31(15): 4249-4258, May 2010.
International Search Report and Written Opinion issued for International Application No. PCT/US2018/061862 dated Feb. 11, 2019.
Lu et al., "Controlled release of transforming growth factor β1 from biodegradable polymer microparticles," *J Bio Mater Res*, 50(3): 440-451, Jun. 5, 2000.
Reing et al., "The effects of processing methods upon mechanical and biologic properties of porcine dermal extracellular matrix scaffolds," *Biomaterials*, 31(33): 8626-8633, Nov. 2010.
Rudnicki et al., "Hypoxia inducible factor-dependent regulation of angiogenesis by nitro-fatty acids," *Arteriosclerosis, Thrombosis, and Vascular Biology*, 31(6): 1360-1367, Mar. 31, 2011.
Soletti et al., "A bilayered elastomeric scaffold for tissue engineering of small-diameter vascular grafts," *Acta Biomaterialia*, 6(1): 110-122, Jun. 18, 2009.

* cited by examiner

*Primary Examiner* — Alma Pipic
(74) *Attorney, Agent, or Firm* — Klarquist Sparkman, LLP

(57) ABSTRACT

A construct comprising a dermal extracellular matrix gel, polymer fibers, and microparticles containing a nitro oleic acid agent.

9 Claims, 16 Drawing Sheets

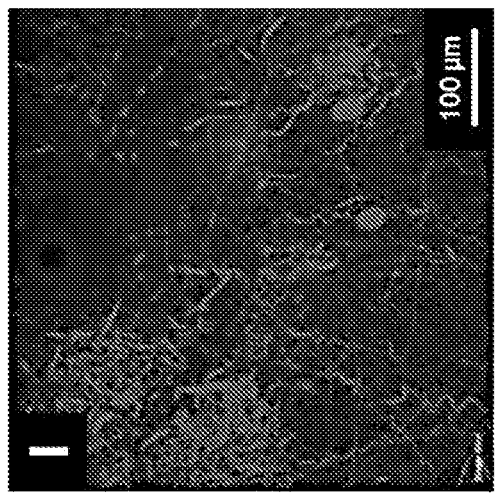
FIG. 2I
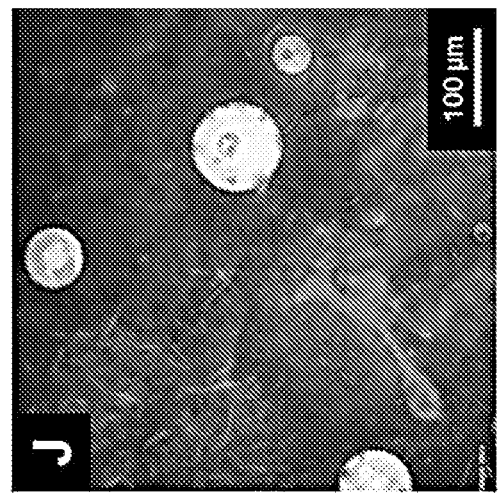
FIG. 2J
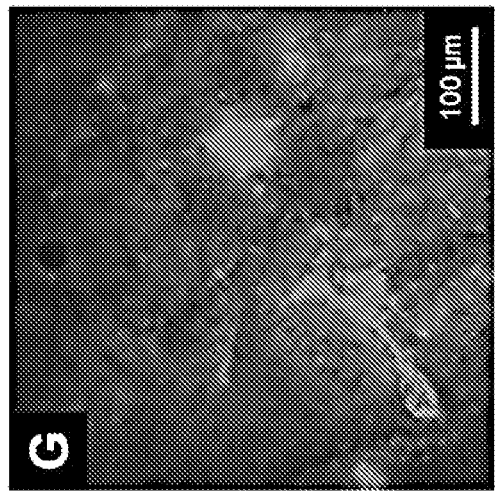
FIG. 2G
FIG. 2H
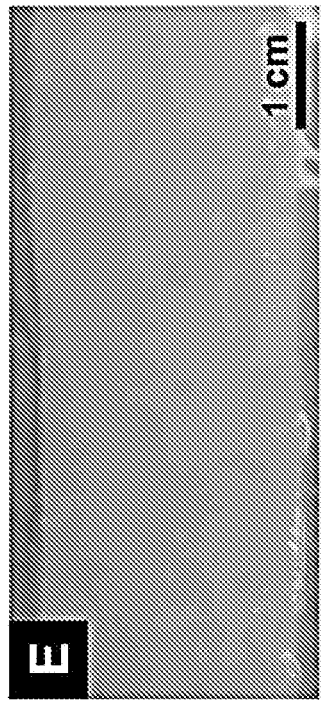
FIG. 2E
FIG. 2F
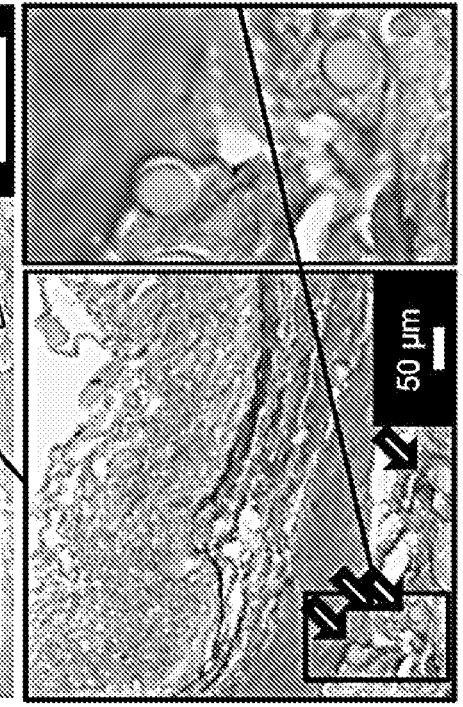

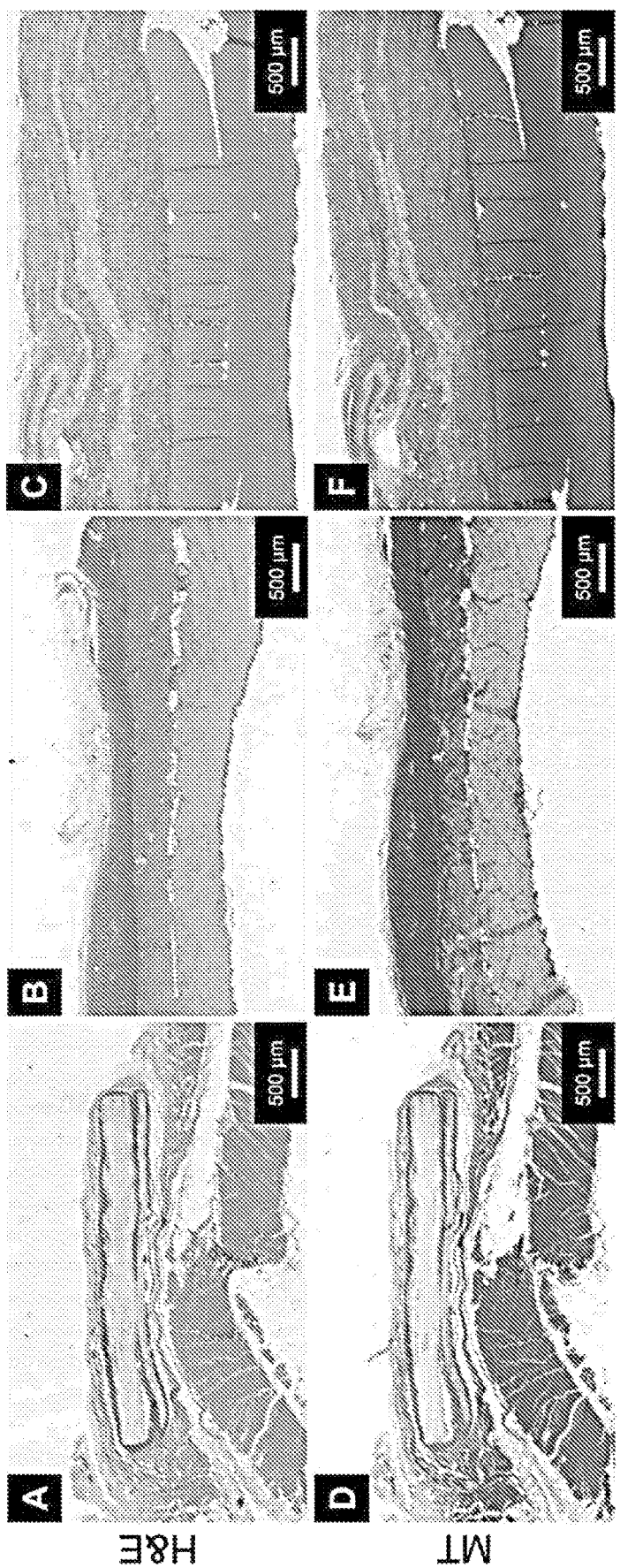

FIG. 5A  
H&E
FIG. 5B  
MT
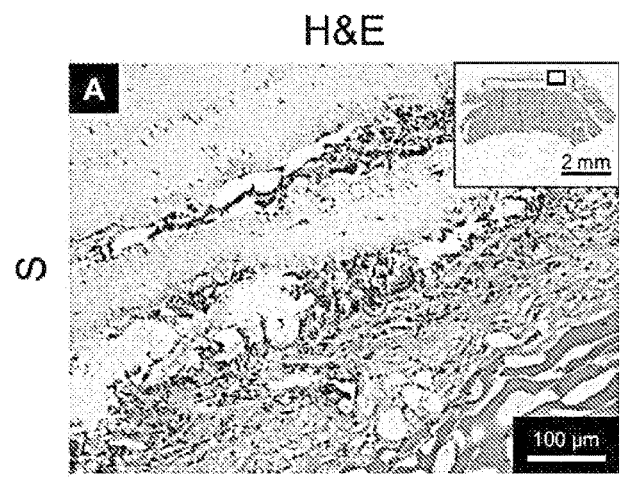
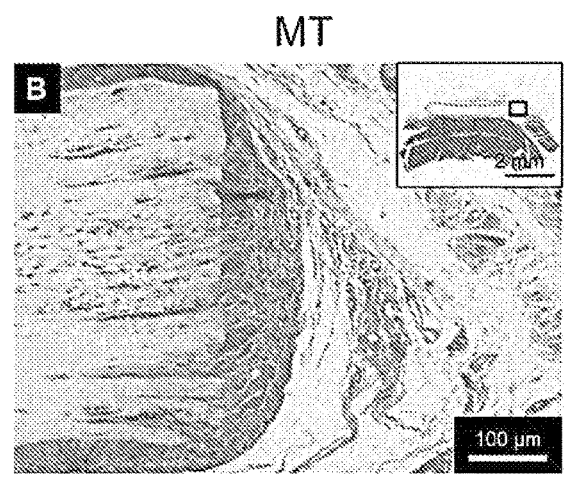
FIG. 5C
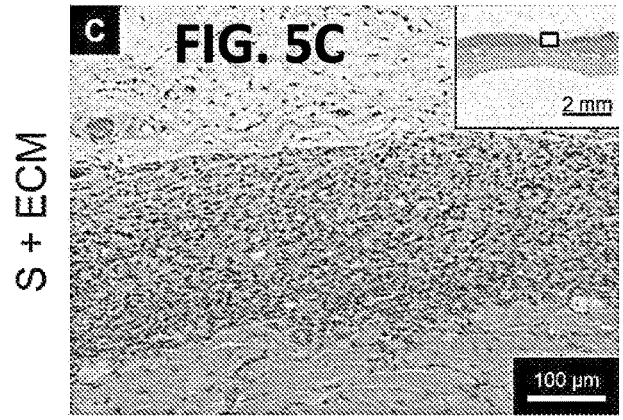
FIG. 5D
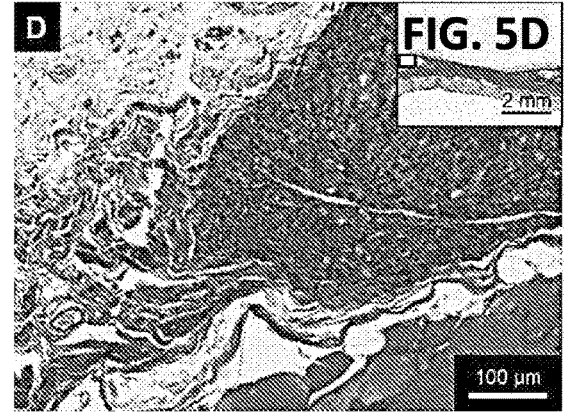
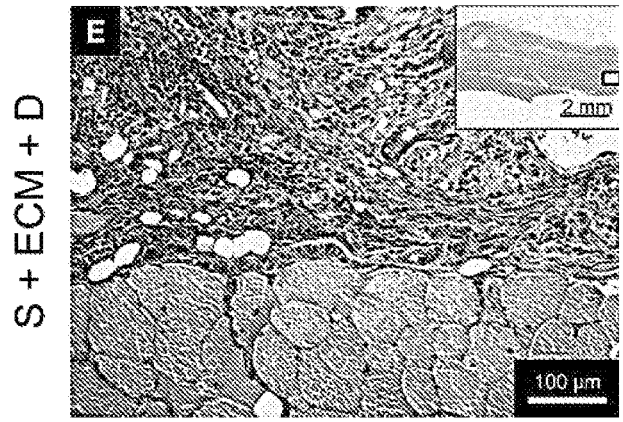
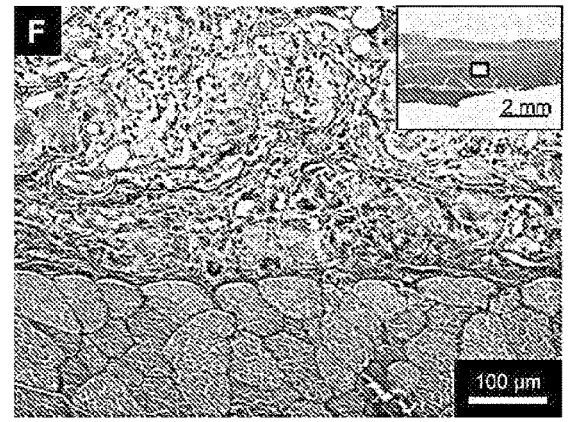
FIG. 5E  FIG. 5F

FIG. 6A
S
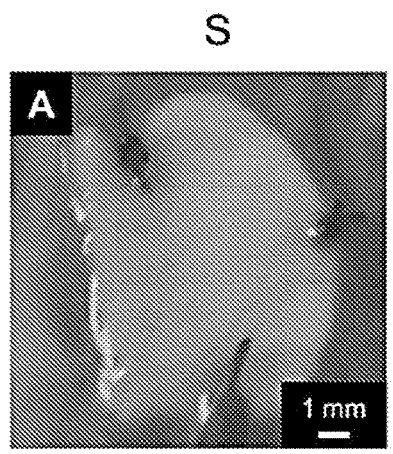
FIG. 6B
S + ECM
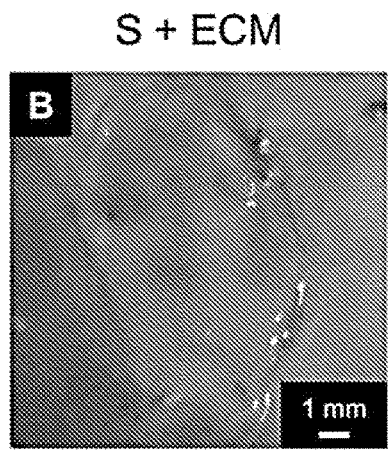
FIG. 6C
S + ECM + D
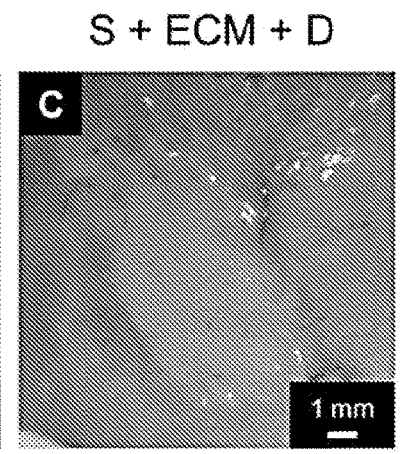
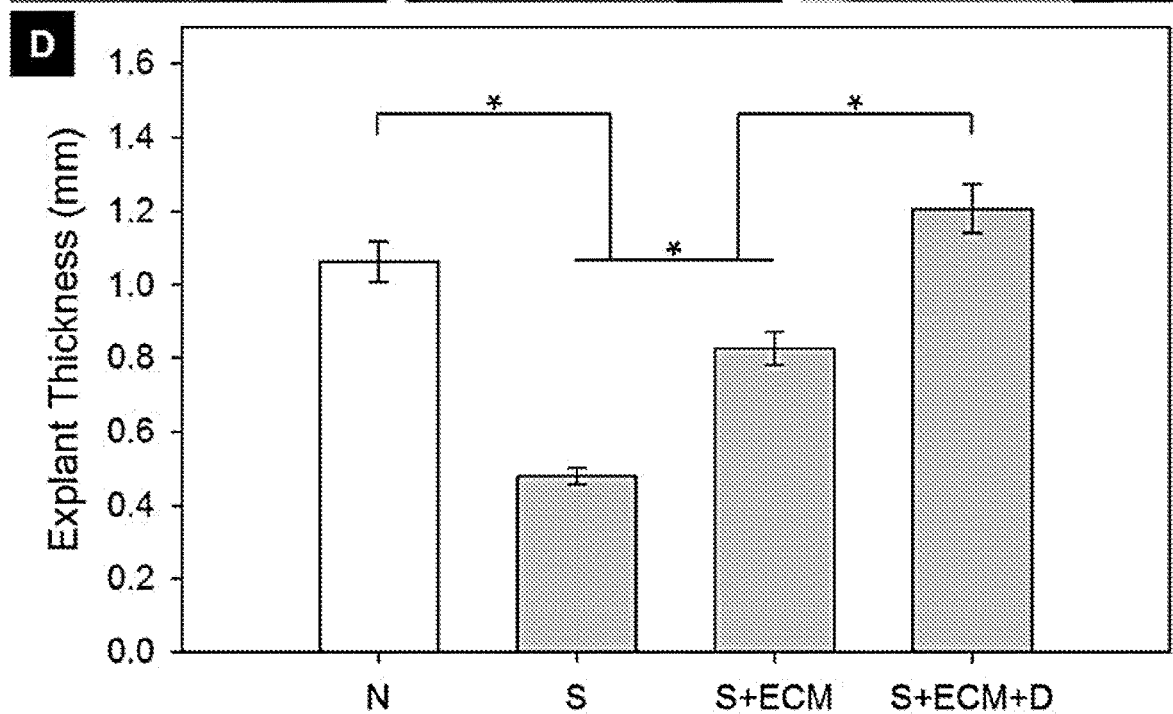
FIG. 6D

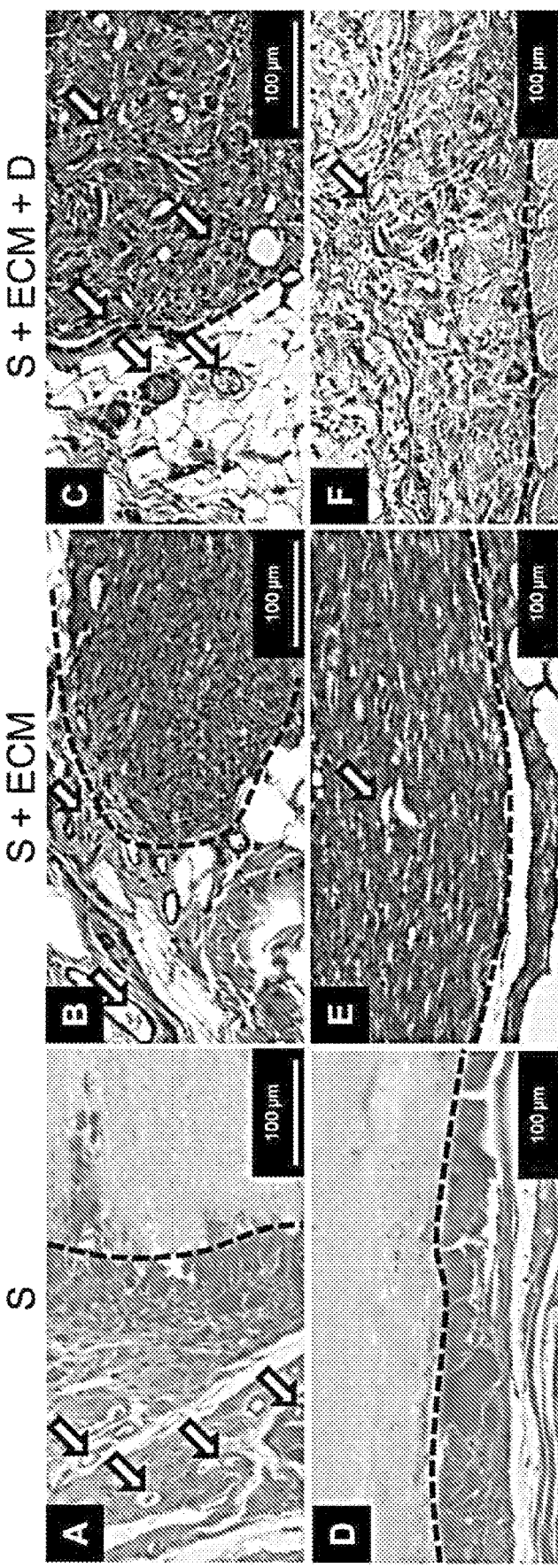

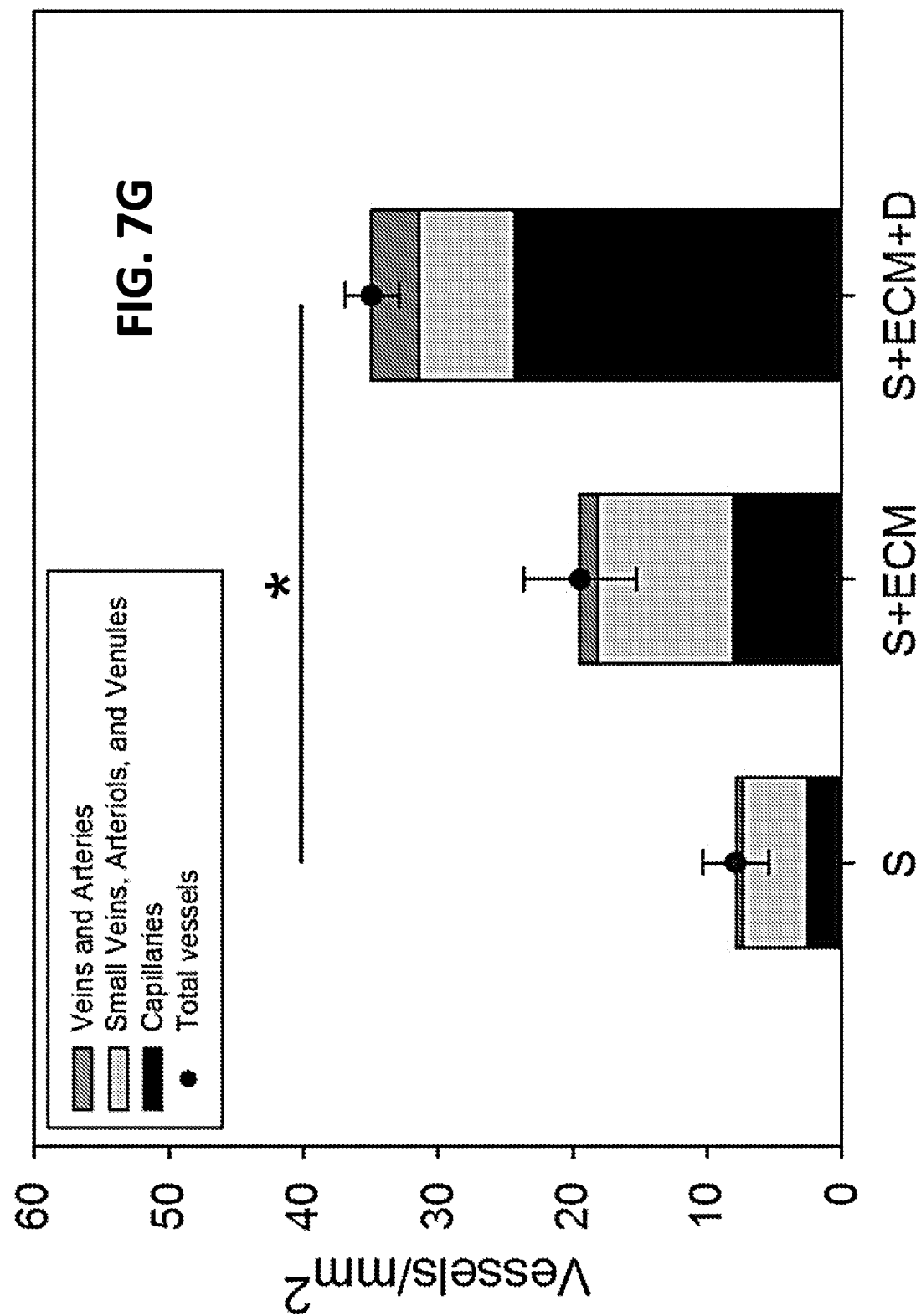

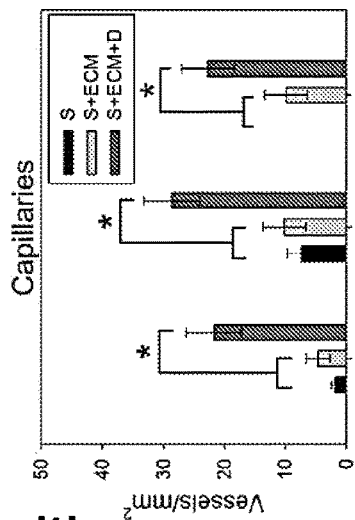
FIG. 8E
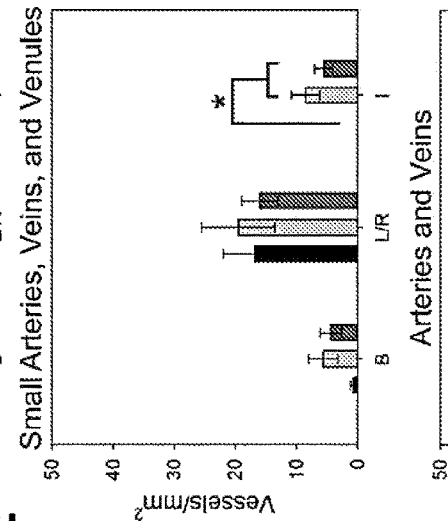
FIG. 8F
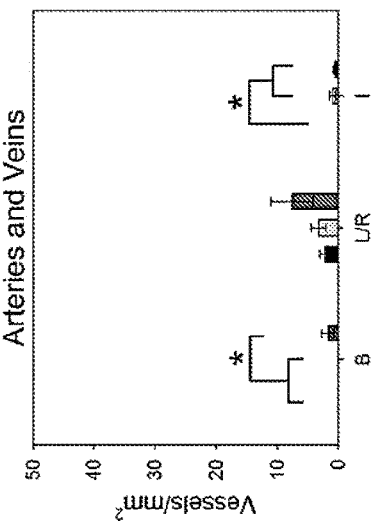
FIG. 8G
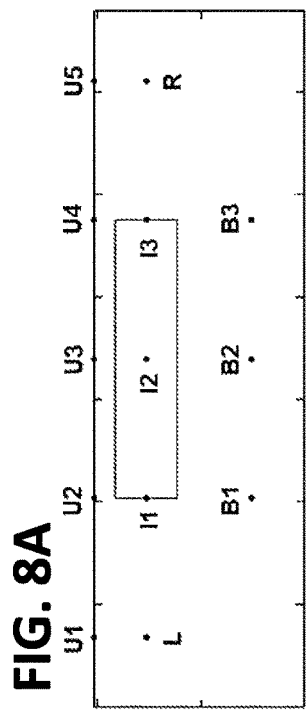
FIG. 8A
FIG. 8B
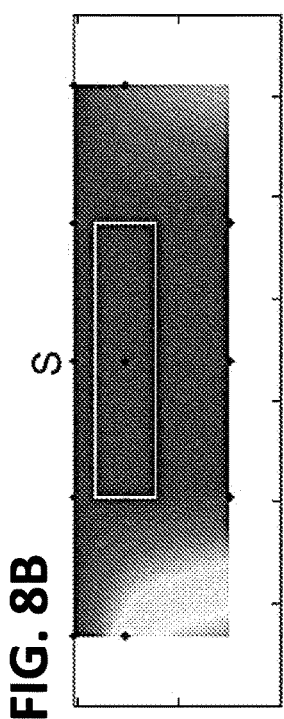
FIG. 8C
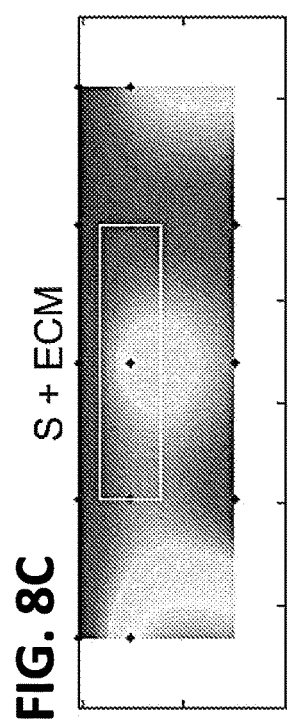
FIG. 8D
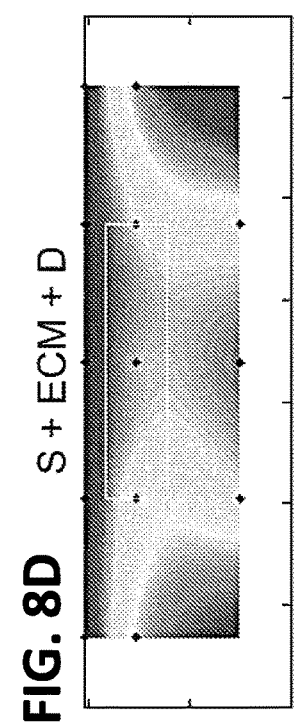

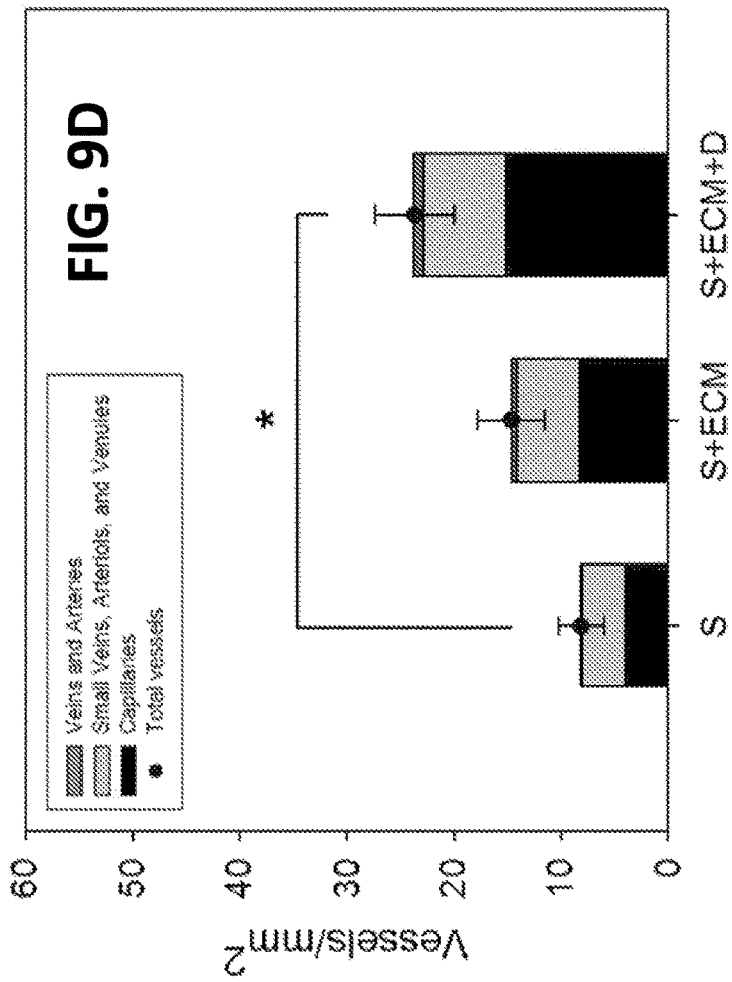

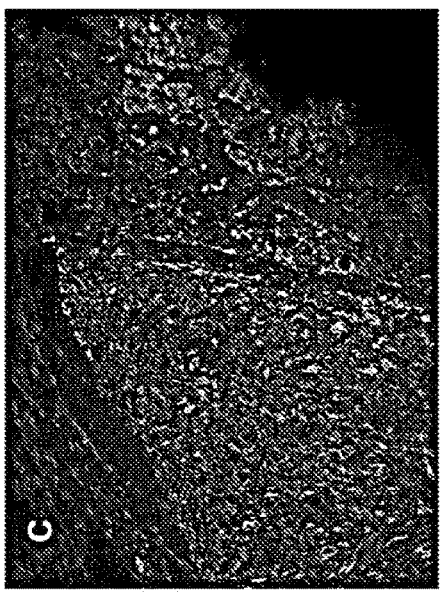
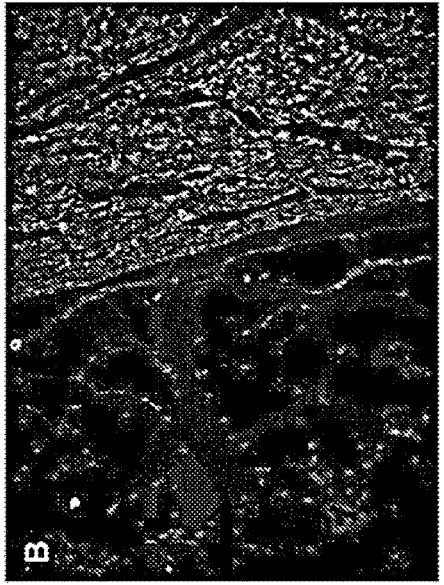
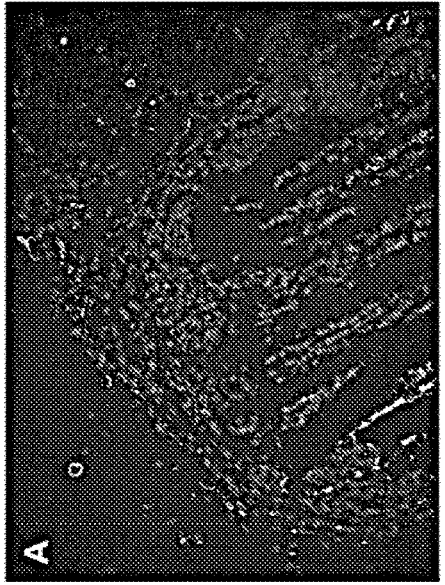
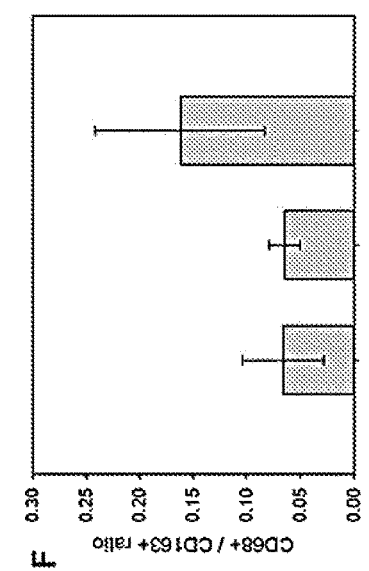
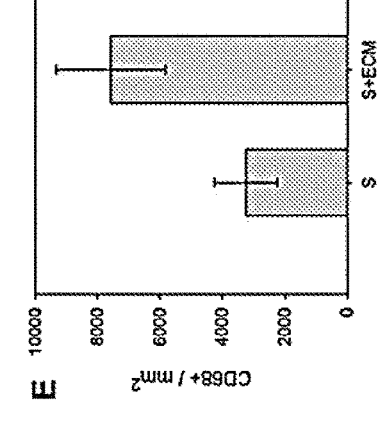
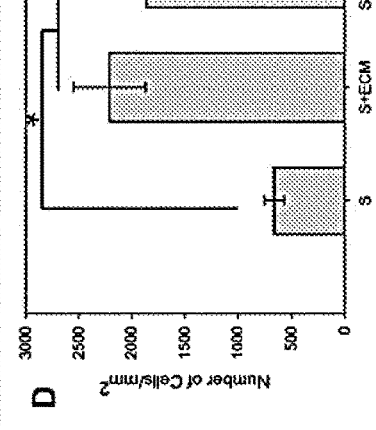

FIG. 11

Table 1| Scaffolds particle density

| | |
|---|---|
| Volume (mm$^3$) | 0.025 |
| Particles (#) | 6.5 ± 1.6 |
| Particles/Volume (#/mm$^3$) | 260 ± 62 |
| NO$_2$OA (pmol/mg) | 31.8 ± 1.8 |

FIG. 12

Table 2| PECUU Characterization

| | $T_g$ (°C) | $T_m$ (°C) | Young's modulus (MPa) | Tensile strength (MPa) | Strain-to-failure (%) |
|---|---|---|---|---|---|
| PECUU | -55 | 13 | 9 ± 1 | 21 ± 2 | 821 ± 73 |

NITRO-OLEIC ACID CONTROLLED RELEASE PLATFORM TO INDUCE REGIONAL ANGIOGENESIS IN ABDOMINAL WALL REPAIR

CROSS-REFERENCE TO RELATED APPLICATIONS

This is the U.S. National Stage of International Application No. PCT/US2018/061862, filed Nov. 19, 2018, which was published in English under PCT Article 21(2), which application in turn claims the benefit of U.S. Provisional Patent Application No. 62/588,830, filed Nov. 20, 2017, which is incorporated by reference herein in its entirety.

ACKNOWLEDGMENT OF GOVERNMENT SUPPORT

This invention was made with government support under Grant Numbers AT006822, HL058115, and HL064937 awarded by the National Institutes of Health. The government has certain rights in the invention.

BACKGROUND

Ventral hernia is one of the most common complications following abdominal surgery. In 2004, more than 1,000 patients died with abdominal wall hernia as the underlying cause. The definitive treatment remains surgical repair. About 115,000 hernia and abdominal wall defect repairs are performed every year in the U.S., producing a consistent healthcare burden and substantially impacting the quality of life for those patients.

Prosthetic materials, either synthetic or from allogenic and xenogenic sources, have increasingly been accepted as a better strategy than direct tissue apposition. This reduced the impact of typical complications such as chronic patient discomfort, surgical site infections or fistulas. In spite of these advances, a number of issues remain unsolved including high hernia recurrence, mesh encapsulation, partial tissue remodeling, mechanical mismatch at the native tissue-implant interface, and reduced vascularity of the implanted volume.

These limitations encouraged a further paradigm shift toward the regenerative medicine/tissue engineering approach where synthetic meshes are combined with cells or with biologic materials, designed to function as temporary tissue surrogates and intended to be gradually replaced by the antagonist action of tissue remodeling and scaffold degradation.

Previous experiences with elastic biodegradable synthetic materials such as poly (ester carbonate) urethane ureas (PECUUs) combined with dermal extracellular matrix (ECM) gels have demonstrated the capacity to improve cellular infiltration, native tissue-prosthesis mechanical interaction, and tissue remodeling. Despite these achievements, tissues that both underwent constructive remodeling and gained sufficient mechanical strength following scaffold implantation have not restored the level of muscle function and vascularity observed in the native healthy abdominal wall. Towards this end, in situ controlled release of angiogenic factors might substantially leverage the clinical relevance of such materials for the reconstruction of the diseased abdominal wall or for a variety of other applications, such as cardiovascular tissue repair and augmentation.

SUMMARY

Disclosed herein is a construct comprising:
a dermal extracellular matrix gel;
polymer fibers; and
microparticles containing a nitro oleic acid agent.

This construct may be used for repairing at least a portion of an abdominal wall of a subject by applying the construct to the portion of the abdominal wall. In certain embodiments, release of the nitro oleic acid agent enhances neovascularization at the portion of the abdominal wall.

The foregoing will become more apparent from the following detailed description, which proceeds with reference to the accompanying figures.

BRIEF DESCRIPTION OF THE DRAWINGS

FIG. 1A) via sonication, FIG. 1B) or 1500 RPM and FIG. 1C) 100 RPM agitator speed. FIG. 1D) $NO_2$-OA in vitro controlled release profiles, effects of microparticle size on release kinetics (n=3). FIG. 1E) microparticle size quantification.

FIGS. 2A-2J. Pre-implantation scaffold structure. Visual and histological scaffold structure comparison for the single layer S group (FIG. 2A-FIG. 2B), for the double layer S+ECM group (FIG. 2C-2D) and for the PLGA microparticle integrated S+ECM+D group (FIG. 2E-FIG. 2F). Higher magnification inset confirmed microparticle or ECM incorporation. Multi-photon image stacks (500×500×100 m): (FIG. 2G) integrated PLGA microparticles and (FIG. 2H) a composite image stack showing a combination of PECUU electrospun fibers and PLGA microparticles for the S group. (FIG. 2I) $NO_2$-OA loaded integrated PLGA microparticles and (FIG. 2J) composite image stack showing PECUU electrospun fibers, dermal ECM gel and $NO_2$-OA loaded PLGA microparticles for the S+ECM+D group. Arrows in FIG. 2B, FIG. 2F, FIG. 2H, and FIG. 2G indicate the PLGA microparticles.

FIG. 3A) Scaffold biaxial mechanics characterization (LD and CD indicated the rat longitudinal and circumferential directions respectively) showed, for a given mandrel velocity, no differences were introduced by microparticle incorporation (S) when compared to the ECM integrated group (S+ECM). Comparison with native rat abdominal wall planar mechanics showed the capacity to duplicate physiologically relevant values of anisotropy (n=5). FIG. 3B) Controlled release profile for the S+ECM+D group in lipase solution at 37° C. up to one month, (n=3).

FIGS. 4A-4H. Histological assessment, full cross sections. H&E and MT staining of 8 week explants for the groups: (FIGS. 4A, 4D) S; (FIGS. 4B, 4E) S+ECM, and (FIGS. 4C, 4F) S+ECM+D. Both qualitative (FIGS. 4A-4F) and quantitative observation (FIG. 4H) showed reduced fibrous encapsulation and higher cellular infiltration for the S+ECM and S+ECM+D groups when compared to the S group. (FIG. 4G) examples of collagen/scar area segmentation performed by the developed algorithm. Dotted line indicates the visible part of the scaffold perimeter, n≥3/ group.

FIGS. 5A-5F. Histological assessment, high magnification. H&E and MT staining of 8 week explants for the groups: (FIGS. 5A, 5B) S, (FIGS. 5C, 5D) S+ECM, and (FIGS. 5E, 5F) S+ECM+D. Qualitative assessment of high magnification (200×) cross sections at the explants—scaffold interface confirmed higher cellular infiltration for the S+ECM and S+ECM+D groups when compared to the S group. Top right box indicates the high magnification field of view position (yellow box) with respect to the whole explants. Dotted line indicates the visible part of the scaffold perimeter.

FIGS. 6A-6D. Explants thickness. Visual inspection for the groups: (FIG. 6A) S, (FIG. 6B) S+ECM, (FIG. 6C) S+ECM+D. (FIG. 6D) full wall thickness comparison with group N representing the healthy rat abdominal wall thickness.

FIGS. 7A-7G. Blood vessel morphological assessment via MT staining Representative MT staining of 8 week cross sections at left (L) and right edge (R), below (B) and inside (D) the abdominal wall explants for the groups: (FIGS. 7A, 7D,) S, (FIGS. 7B, 7E) S+ECM, (FIGS. 7C, 7F) S+ECM+D. Blood vessels number and type quantification. FIG. 7G shows the results of the quantitative analysis.

FIGS. 8A-8G. Blood vessel morphological assessment via immunofluorescence staining Representative DAPI (blue), CD31 (green) and αSMA (red) co-staining of 8 week cross sections (region I) for the groups: (FIG. 8A) S, (FIG. 8B) S+ECM, (FIG. 8C) S+ECM+D. (FIG. 8D) blood vessels number and type quantification. FIGS. 8E-8G show quantitative measurement.

FIGS. 9A-9D. Blood vessel topological assessment. (FIG. 9A) Schematic of the analyzed explants area. MT cross sections were imaged at 200x covering the region occupied by the implanted patch (inside: I1, I2, I3), the region underneath (below: B1, B2, B3) and the edges where the material is sutured to the native tissue (left and right: L, R). The solid line around points I1-I3 indicated the approximated border of scaffold whereas each point corresponded to the geometrical center of each image, and U1-U5 represented the upper border of the explants. Total vessel/mm$^2$ spatial distribution was provided in (FIG. 9A) for group S, (FIG. 9B) for S+ECM, and (FIG. 9C) for S+ECM+D. Each color map represented the mean of the spatial distribution for blood vessels detected on n≥5 animals. (FIG. 9D) offered the quantitative topological assessment for arteries and veins.

FIGS. 10A-10F. Macrophage infiltration. Representative DAPI (blue), CD68 (green), and CD163 (red) co-staining of 8 wk cross sections (region I) for the groups: (FIG. 10A) S, (FIG. 10B) S+ECM, (FIG. 10C) S+ECM+D. (FIG. 10D) cell infiltration via DAPI staining (FIG. 10E) macrophage infiltration, quantification performed on CD68+cells. (FIG. 10F) macrophage polarization via CD68+/CD163+ratio.

FIG. 11 is a table showing the particle density in the scaffold.

FIG. 12 is a table showing characteristics of the polymer (PECUU).

DETAILED DESCRIPTION

Terminology

Figure 1C:
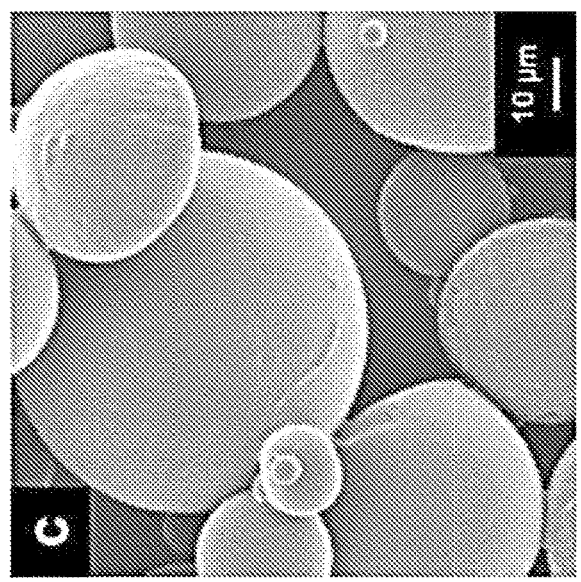
FIGS. 1A-1E. Controlled release in vitro characterization. PLGA microparticle size obtained at different processing conditions.
Figure 1B:
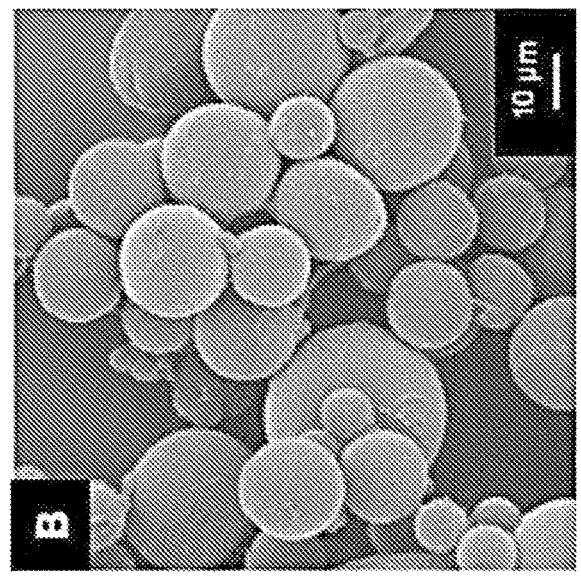
Figure 1A:
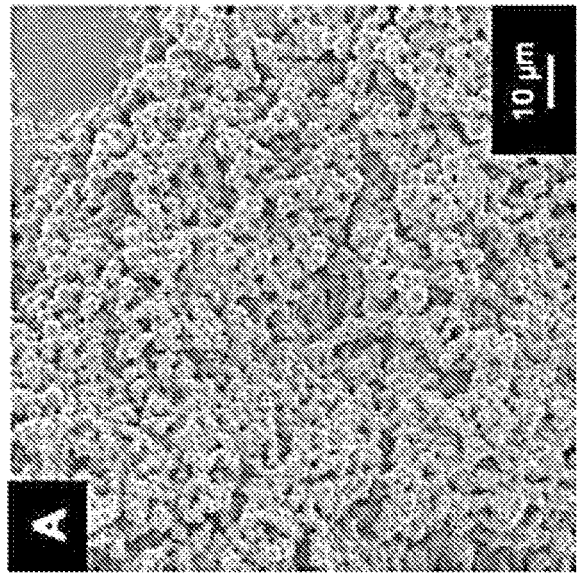

The following explanations of terms and methods are provided to better describe the present compounds, compositions and methods, and to guide those of ordinary skill in the art in the practice of the present disclosure. It is also to be understood that the terminology used in the disclosure is for describing particular embodiments and examples only and is not intended to be limiting.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkyl" refers to a branched or unbranched saturated hydrocarbon group, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$) alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$) cycloalkyl ($C_1$-$C_6$) alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$) alkoxy can be methoxy, ethoxy, propoxy, isopropoxy, butoxy, iso-butoxy, sec-butoxy, pentoxy, 3-pentoxy, or hexyloxy; ($C_2$-$C_6$) alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1- hexenyl, 2-hexenyl, 3-hexenyl, 4-hexenyl, or 5-hexenyl; (C2-C6) alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1- hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; (C2-C6)alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

Electrophilic fatty acid nitro-alkene derivatives (nitro-fatty acids, $NO_2$-FA) are endogenously generated by pro-oxidative inflammatory reactions and the acidic gastric milieu during digestion. The electrophilic nature of $NO_2$-FA induces reversible post-translational modification of cysteine-containing proteins, many regulating metabolic and inflammatory signaling cell signaling and gene expression responses. The beneficial and anti-inflammatory effects of $NO_2$-FA have been shown in various animal models of disease and soon nitro-oleic acid ($NO_2$-OA) is entering FDA phase II clinical trials for the treatment of chronic renal and pulmonary diseases. Notably, $NO_2$-FA induces both endothelial nitric oxide synthase gene and protein expression (Khoo FRBM) and promote angiogenesis via an NO-dependent activation of HIF-1α under hypoxic conditions. While numerous studies have combined scaffold systems with the controlled release of angiogenic factors (e.g. IGF-I, HGF, bFGF), pleiotropic signaling mediators such as $NO_2$-FA have not been applied in this manner. Further, the evaluation of angiogenic factor controlled release in the application of a temporary scaffold to facilitate abdominal wall tissue reconstruction, and more broadly the evaluation of angiogenesis itself, has been addressed by only qualitative or semi-quantitative methods.

Disclosed herein are micro-fibrous poly(ester carbonate) urethane urea (PECUU) scaffolds integrated with a hydrogel derived from decellularized porcine dermis and poly(lactic-co-glycolic acid) (PLGA) microspheres loaded with 10-nitro-9-transoctadecenoic acid ($NO_2$-OA). These scaffolds were utilized to repair a rat abdominal wall partial thickness defect. Although not bound by any theory, it is believed that the nitro-fatty acid release would facilitate increased angiogenesis at the 8-week end-point. The quantification of neovascularization was of primary interest, using novel methodologies to assess vessel morphology and spatial distribution, and several other parameters were evaluated to assess the repaired abdominal wall defects, including the foreign body response and cellular ingrowth. Results showed that $NO_2$-OA release was associated with significantly improved regional angiogenesis in the model.

In certain embodiments, the fibrous scaffold may be made from polyolefin (e.g., polyalkene), polyester, polycarbonate, polyanhydride, polyether, polyurea, polyurethane, polyketone, and fluoropolymer. Non-limiting examples of biocompatible, bioedegradable, elastomeric (co)polymers include: poly(ester urethane) urea (PEUU), poly(ether ester) urethane urea (PEEUU), poly(ester carbonate) urethane urea (PECUU) and poly(carbonate) urethane urea (PCUU). In general, useful (co) polymers include without limitation: monomers of alpha-hydroxy acids; polylactides, such as poly(lactide-coglycolide), poly(L-lactide-co-caprolactone), polyglycolicacid, poly(DL-lactide-co-glycolide) , poly (L-lactide-co-DL-lactide) ; polyesters including polyhydroxybutyrate, polyhydroxyvalerate, polydioxanone and polyglactin; polylactones including polycaprolactone; polycarbonates, polyglyconate, poly(glycolide-co-trimethylene carbonate), poly(glycolideco-trimethylene carbonate-co-dioxanone); and olyurethanes, poly(ester urethane) urea.

In certain embodiments, the hydrogel may be made from a gel-forming substance such as carboxymethylcellulose, polyacrylic acid, agar, arabic gum, alginate, alginic acid, gelatin, starch, methylcellulose, hydroxyethylcellulose, or tragacanth gum, or a mixture thereof.

In certain embodiments, the scaffold may be 0% rich polymer layer—100% ECM/gel rich layer to 100% rich polymer layer—0% ECM/gel rich layer.

In certain embodiments, the nitroalkene fatty acid is a compound that includes at least one carbon-carbon double bond and at least one nitro group. Certain nitroalkene fatty acids are described, for example, in U.S. Pat. No. 7,776,916.

One illustrative embodiment of a nitroalkene fatty acid is of formula I:

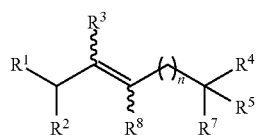

wherein $R^1$ is hydrogen, $C_1$-$C_{24}$ alkyl, $C_1$-$C_{24}$ alkenyl, or $C_1$-$C_{24}$ alkynyl;
$R^2$, $R^3$, $R^7$, and $R^8$ are each independently, hydrogen, $NO_2$, OH, or OOH;
$R^4$ is a terminal $COOR^6$ group, wherein $R^6$ is hydrogen, $C_1$-$C_{24}$ alkyl, or a pharmaceutically acceptable counterion;
$R^5$ is hydrogen or $R^4$ and $R^5$ collectively form=$C(R^9)$ ($R^{10}$), wherein $R^9$ comprises $C_1$-$C_{24}$ alkyl, $C_1$-$C_{24}$ alkenyl, or $C_1$-$C_{24}$ alkynyl, wherein $R^9$ is a terminal $COOR^6$ group, and $R^{10}$ is hydrogen, $NO_2$, OH, or OOH;
n is from 1 to 24; and
wherein the nitroalkene fatty acid includes at least one $NO_2$ group.

In certain embodiments, $R^1$ is $C_1$-$C_{24}$ alkyl, more particularly $C_3$-$C_{20}$ alkyl.
In certain embodiments, $R^2$ is hydrogen.
In certain embodiments, one of $R^3$ or $R^8$ is $NO_2$ and the other of $R^3$ or $R^8$ is hydrogen.
In certain embodiments, n is 3 to 20.
In certain embodiments, $R^4$ is —COOH.
In certain embodiments, $R^5$ is hydrogen.
In certain embodiments, $R^7$ is hydrogen.
In certain embodiments, the nitroalkene fatty acid is of formula II:

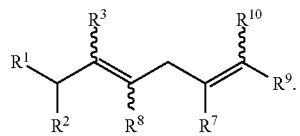

wherein $R^1$, $R^2$, $R^3$, $R^7$, $R^8$, $R^9$ and $R^{10}$ are the same as in formula I.

In certain embodiments, the nitroalkene fatty acid is of formula III:

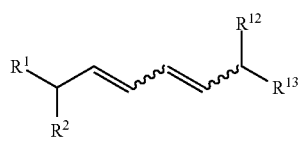

wherein $R^1$ is $C_1$-$C_{24}$ alkyl, $C_1$-$C_{24}$ alkenyl, or $C_1$-$C_{24}$ alkynyl;
$R^2$ and $R^{12}$ are each independently, hydrogen, $NO_2$, OH, or OOH; and
$R^{13}$ is a terminal $COOR^6$ group, wherein $R^6$ is hydrogen, $C_1$-$C_{24}$ alkyl, or a pharmaceutically acceptable counterion, and the nitroalkene fatty acid includes at least one $NO_2$ group.

The polymers for the microparticle may be bioerodible polymers so long as they are biocompatible. Preferred bio-erodible polymers are polyhydroxyacids such as polylactic acid and copolymers thereof. Illustrative polymers include poly glycolide, poly lactic acid (PLA), and poly (lactic-co-glycolic acid) (PLGA). Another class of approved biodegradable polymers is the polyhydroxyalkanoates.

Other suitable polymers include, but are not limited to: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly (methyl acrylate), poly(isopropyl acrylate), poly(isobutyl acrylate), poly(octadecyl acrylate), polyethylene, polypropylene polyethylene glycol), poly(ethylene oxide), poly(ethylene terephthalate), poly(vinyl alcohols), poly(vinyl acetate), poly vinyl chloride polystyrene, polyvinylpyrrolidone, alginate, poly(caprolactone), dextran and chitosan.

In certain embodiments, the amount of agent loaded into the microparticles may be 1 to 1000 pmol/mg, more particularly 0-100 pmol/mg.

The percent loading of an agent may be increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs. Alternatively, the polymer can be made more hydrophilic, for example, by introducing carboxyl groups onto the polymer. A combination of a hydrophilic drug and a hydrophobic drug can be encapsulated in microparticles prepared from a blend of a more hydrophilic PLGA and a hydrophobic polymer, such as PLA.

Illustrative polymers include, but are not limited to, poly(D,L-lactic-co-glycolic acid) (PLGA, 50:50 lactic acid to glycolic acid ratio, $M_n$=10 kDa, acid-terminated, referred to as 502H); poly(D,L-lactic-co-glycolic acid) (PLGA, 50:50 lactic acid to glycolic acid ratio, $M_n$=25 kDa, acid-terminated, referred to as 503H); poly(D,L-lactic-co-glycolic acid) (PLGA, 50:50 lactic acid to glycolic acid ratio, $M_n$=30 kDa, acid-terminated, referred to as 504H); poly(D, L-lactic-co-glycolic acid) (PLGA, 50:50 lactic acid to glycolic acid ratio, $M_n$=35 kDa, ester-terminated, referred to as 504); and poly(D,L-lactic-co-glycolic acid) (PLGA, 75:25 lactic acid to glycolic acid ratio, $M_n$=10 kDa, referred to as 752).

In certain embodiments, the polymer microparticles are biodegradable.

In certain embodiments, the agent-loaded microparticles may have an average diameter of 0.1 to 200 μm, more particularly 10-50 μm.

In certain embodiments, the amount of agent-loaded microparticles incorporated into the scaffold may range from 0.05 to 50 nmol/mg, more particularly 0.5-5 nmol/mg.

The abdominal wall patch disclosed herein combines the benefits of biohybrid biomaterials with the controlled release of $NO_2$-OA for enhanced regional angiogenesis. Results documented $NO_2$-OA release significantly enhanced regional angiogenesis in a rat abdominal wall defect model. More broadly, this three components scaffold design strategy including (I) dermal extracellular matrix (ECM) gel, (II) polymeric fibers and (III) PLGA microparticles potentially enables A) to incorporate a bioactive component, B) to tune scaffold degradation by modifying the polymeric matrix chemistry, C) to modulate scaffold mechanics by changing the electrospinning mandrel kinematic, and D) to control drug release by changing microparticle morphology.

In certain embodiments, the scaffolds disclosed herein demonstrate:

A. $NO_2$-OA release significantly enhanced regional angiogenesis in a rat abdominal wall defect model;
B. $NO_2$-OA release significantly increased wall thickness in a rat abdominal wall defect model;
C. $NO_2$-OA release significantly reduce fibrotic response in a rat abdominal wall defect model;
D. developed a scaffold platform capable to simultaneously incorporate a bioactive component;
tune scaffold degradation by modifying the polymeric matrix chemistry;
modulate scaffold mechanics by changing the electrospinning mandrel kinematic;
control drug release by changing microparticle morphology.

The abdominal wall patch strategy reported herein demonstrate the benefits of a biohybrid biomaterials approach combined with the controlled release of an angiogenesis facilitating mediator ($NO_2$-OA). Enhanced angiogenesis was demonstrated by a newly described method to spatially quantify vascularization. The three components of the employed composite scaffold design strategy (ECM gel, polymeric fibers and $NO_2$-OA loaded PLGA microparticles) enable a tuning of biomaterial performance characteristics. Scaffold degradation and mechanics can be modified with the polymeric component and processing parameters, while the controlled release characteristics of the synthetic endogenous mediator homolog can be tuned by changing microparticle/drug loading characteristics. The overall system provides a biomaterial design approach applicable to other tissue augmentation and support settings.

EXAMPLES

Materials and Methods

Polymer Synthesis, Dermal ECM Extraction and Gel Preparation

PECUU was synthesized starting from polycaprolactone-diol (PCL, $M_n$=2000, Sigma), polyhexamethylene carbonate-diol (PHC, $M_n$=2000, Sigma) and butyl diisocyanate (BDI, Sigma), putrescine was adopted as a chain extender following the protocol described in Hong, Y et al. Tailoring the degradation kinetics of poly(ester carbonate urethane) urea thermoplastic elastomers for tissue engineering scaffolds. Biomaterials 31, 4249, 2010. The (PCL+PHC):BDI: putrescine and PCL/PHC molar ratios were 1:2:1 and 1:1 respectively. Thermal properties were measured by differential scanning calorimetry (DSC, DSC-60, Shimazu). Samples were heated to 200° C. to erase thermal history, then cooled to −150° C., and heated again to 200° C. All heating and cooling rates were 10° C./min. The polymer utilized had a $T_g$ of −55° C. and a $T_m$ of 13° C. Based on uniaxial tensile testing, Young's modulus was 9 ±1 MPa, tensile strength 21±2 MPa and the strain to failure was 821±73%.

Porcine dermal extracellular matrix (ECM) was prepared as reported previously (Reing et al. The effects of processing methods upon mechanical and biologic properties of porcine dermal extracellular matrix scaffolds. Biomaterials 31, 8626, 2010). In brief, full thickness skin from the dorsolateral flank of market weight (~260 pounds) pigs was harvested. Subcutaneous fat, connective tissue and epidermis were mechanically removed. The obtained dermis was subjected to sequential immersion in a vortex shaker at 600 RPM in solutions including: 0.25% trypsin, 70% ethanol, 1% TritonX-100 in 0.26% ethylenediaminetetraacetic acid-tetrasodium salt (EDTA)/0.69% Tris, and 0.1% peracetic acid/4% ethanol. The resulting decellularized tissue samples were then lyophilized and milled into a powder with a commercial Waring™ blender and a Wiley Mill. The powder was further processed with 1 mg/mL pepsin (P7012 Sigma) in 0.01 M HCL. Finally, each 0.75 mL of ECM digest was neutralized with 10×phosphate-buffered saline (PBS), 0.1 N NaOH (0.075 ml) and 1×PBS (0.092 ml) and produced 1 mL of 15 mg/mL ECM solution.

Microparticle Fabrication

Poly-lactic-co-glycolic acid (PLGA) microparticles were fabricated by a double emulsion technique originally introduced in Lu et al. Controlled release of transforming growth factor betal from biodegradable polymer microparticles. J Biomed Mater Res 50, 440, 2000. For the oil component 0.2 g of PLGA (50:50 wt ratio, 30-60k $M_w$, Sigma) was dissolved in 4 mL of dichloromethane (5% w/v, Sigma), whereas 300 µL of 1% PBS/distilled water solution and 60 mL of 2% PBS/polyvinyl alcohol solution were utilized as water one and water two components respectively. Similarly, the drug was encapsulated in the microparticles by mixing 8.57 µL of 10-nitro-9-trans-octadecenoic acid ($NO_2$-OA) with 35 mM to the water one component targeting a final molarity of 1 M. The oil-water one emulsion was then created by vortexing for 1 min. Different particle sizes (FIGS. 1A-1C, 1E) were obtained by setting the agitator at rotation speeds of 1000 and 1500 RPM or by immersing the oil-water beaker in the sonicator bath (Quantrex 90, L&R, Keamy N.J.). Solvent evaporation for 6 hrs was followed by three sequential distilled water washes with centrifugation (15,000 xg for 5 min). Freeze drying for 24 hr completed the process, after which the microparticles were collected and stored at −20° C. prior to integration in the abdominal wall patch.

Abdominal Wall Patch Fabrication

Figures 2A, 2B, 2C, 2D:
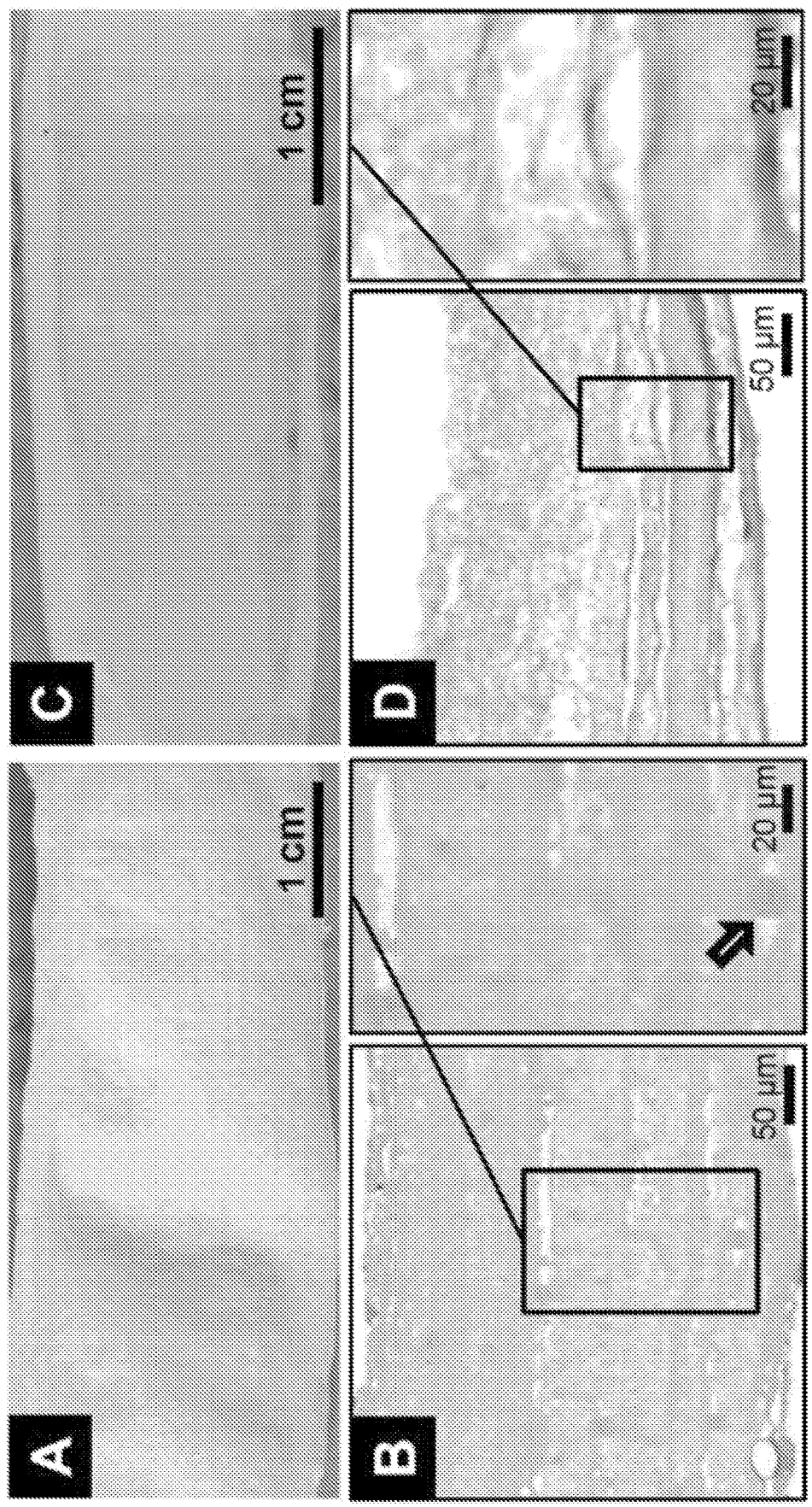

Abdominal wall patches were processed by the two stream electrospinning protocol illustrated in D'Amore et al. Bi-layered polyurethane—Extracellular matrix cardiac patch improves ischemic ventricular wall remodeling in a rat model. Biomaterials 107, 1, 2016, which was modified to incorporate the microparticles into the scaffold volume. Three types of patches were fabricated (FIG. 2): PECUU electrospun single layer scaffold with PLGA microparticles not loaded with $NO_2$-FA (S), PECUU-ECM bi-layered scaffold (S+ECM), and PECUU-ECM bi-layered scaffold with integrated PLGA microparticles loaded with $NO_2$-OA (S+ECM+D). Hexafluoroisopropanol (HFIP, 12% w/v) was utilized to dissolve the PECUU. A 114 mm diameter cylinder was adopted as an electrospinning target charged at −4 kV, rotating at 750 RPM and translating longitudinally at 0.15 cm/s. The deposition area (4.5 cm in width) was confined by electrical insulating tape and reduced rastering span (6 cm).

The single layer scaffold was fabricated via wet electrospinning (Hashizume et al. Morphological and mechanical characteristics of the reconstructed rat abdominal wall following use of a wet electrospun biodegradable polyurethane elastomer scaffold. Biomaterials 31, 3253, 2010) using the following electrospinning processing variables, for stream one (polymer): voltage 13 kV, gap distance 10 cm, flow rate 20 mL/hr. For stream two (PBS) electro-spray conditions were: 8 kV, 4 cm gap and flow rate of 1.35 mL/min. The PBS stream (54 ml) was supplemented with empty PLGA microparticles (170 ±40 mg). Total deposition time for all the groups was 40 min.

For the bi-layer scaffolds in groups S+ECM and S+ECM+D the first layer (polymer rich) was fabricated using the same processing conditions described above with a deposition time of 20 min. The remaining 20 min were utilized to form the scaffold second layer (ECM rich), total fabrication time was 40 min. For the S+ECM the second stream electro-sprayed 15 mg/mL ECM solution with an increased flow rate of 1.5 mL/min while, gaps, voltages and mandrel kinematics remained unmodified.

Processing conditions for the S+ECM+D group were identical to the S+ECM group with the only exception of the ECM solution (30 mL) which was supplemented with the $NO_2$-OA loaded PLGA microparticles (173 ±23 mg). Based on a slower release kinetic, the larger diameter microparticles, fabricated at 1000 RPM as described above, were utilized for the animal model.

Finally, S-ECM and S-ECM-D patches were incubated at 37° C. for 45 min to induce ECM solution transition to a gelled state. Next, 6 mm diameter circular patches were obtained by a surgical punch. The stiffer scaffold direction was identified by cutting with a surgical blade one edge of the patch parallel to the mandrel tangential speed direction. Metallic parts and tools utilized in the scaffold fabrication and preparation were sterilized. Each side of the generated abdominal patches were sterilized with UV light for 30 min prior to implantation, which was performed within 12 hr of fabrication.

Controlled Release In Vitro Characterization

Figure 1D:
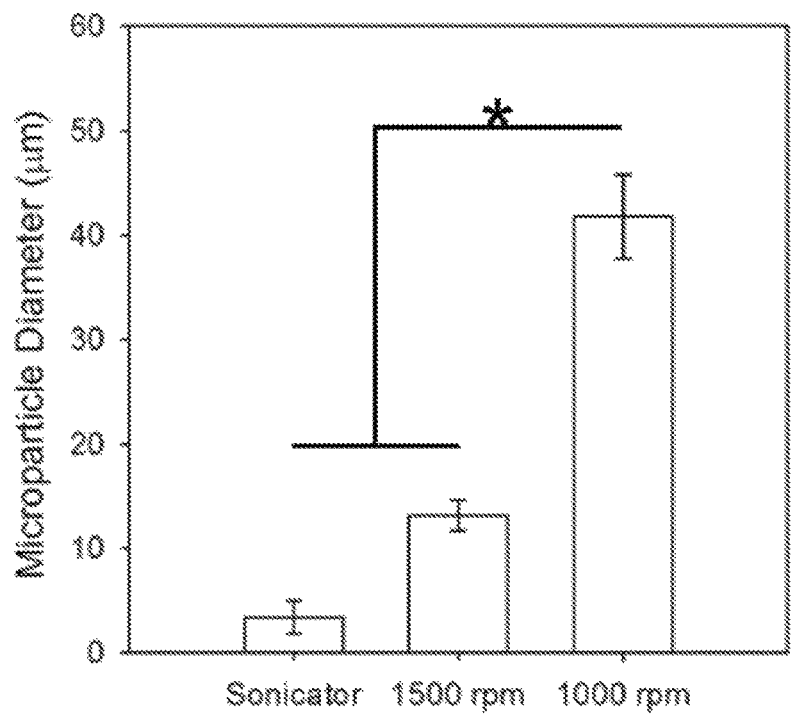
Figure 1E:
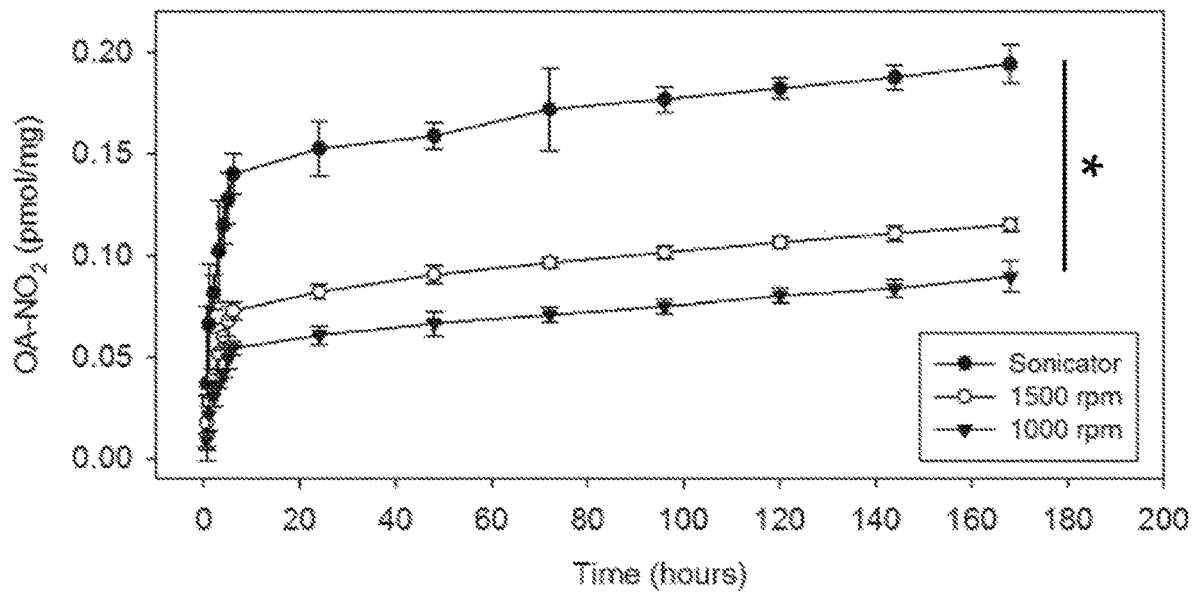

In order to quantify the impact of fabrication conditions, and more specifically agitator speed and sonication on PLGA microparticle morphology, scanning electron microscopy (SEM) was utilized. Microparticles were sputter coated with Pd/Au and imaged (grayscale, 8-bit) with SEM (JEOL JSM6330F), NIH Image J was then adopted to quantify microparticle diameter (FIG. 1E).

Extraction of $NO_2$-OA and Controlled Release In Vitro $NO_2$-OA in microparticles and scaffolds was extracted by dissolving the samples in 200 µL, HFIP with 0.5 pmol $NO_2$-$[^{13}C_{18}]$OA internal standard, and extracted three times with 1 mL methanol, each time vortexing and centrifuging at 15,000 xg for 10 min at 4° C. Then, the collected methanol was dried under a stream of nitrogen, reconstituted in 100 µL methanol and analyzed by high performance liquid chromatography-electrospray ionization-tandem mass spectrometry (HPLC-ESI-MS/MS). Controlled release (n=3) of $NO_2$-OA in microparticles (FIG. 1D) and scaffolds (FIGS. 3B) was studied in 50 mM phosphate buffer, pH 7.4 with 0.2 mg/mL porcine lipase at 37° C. Aliquots were collected at various time points, spiked with 15 pmol $NO_2$-$[^{13}C_{18}]$OA, 1 mL acetonitrile was added and then, samples were vortexed, centrifuged and analyzed by HPLC-ESI-MS/MS. At each time point a fresh incubating solution was utilized.

Liquid Chromatography-Mass Spectrometry Analyis of $NO_2$-OA

Analysis of $NO_2$-OA was performed by HPLC-ESI-MS/MS. The chromatographic system consisted of an analytical C18 Luna column (2×20 mm, 5 µm, Phenomenex) with a flow rate of 0.75 mL/min, and a gradient solvent system of water 0.1% acetic acid (solvent A) and acetonitrile 0.1% acetic acid (solvent B). The gradient program was the following: 35-100% solvent B (0-3 min); 100% solvent B (3-4min) followed by 1 min re-equilibration to initial conditions. The mass spectrometry system consisted of an API4000 Q-trap triple quadrupole mass spectrometer (Applied Biosystems, San Jose, Calif.) equipped with an electrospray ionization source (ESI). $NO_2$-OA was analyzed in negative mode with the following parameters: declustering potential (DP)—75V, collision energy (CE)—35 eV, desolvation temperature of 700° C., and a multiple reaction monitoring (MRM) transition 326.3/46. Quantification of $NO_2$-OA in samples was performed by stable isotopic dilution analysis using a $NO_2$-OA calibration curve in the presence of $NO_2$-$[^{13}C_{18}]$OA internal standard (MRM 344.3/46).

Multi-Photon Imaging

Successful integration of PECUU fibers with ECM and microparticles was verified via multiphoton imaging (FIGS. 2G-2J). Samples (n=5, each 10×10 mm) were scanned over a 500×500×100 μm volume with multi-photon microscopy at 740 nm excitation wavelength, 5% laser power, and 12.5 μs/pixel sampling speed. Emission channels utilized for the acquisition were 400±50 nm for second harmonic generation originated by the ECM signal, 525±50 nm for the scaffold fibers and 595±25 nm for the PLGA microparticles. In order to facilitate acquisition in these last two channels, polymer fibers and microparticle signals were enhanced with molecular probes. PECUU was supplemented with FITC when dissolved in HFIP, similarly Red CMTPX (Molecular Probes) previously mixed with 1 mL of dimethyl sulfoxide was added to the PLGA - solvent solution during the creation of emulsion one in the microparticle processing.

Mechanical Testing and Thermal Properties

Figure 3A:
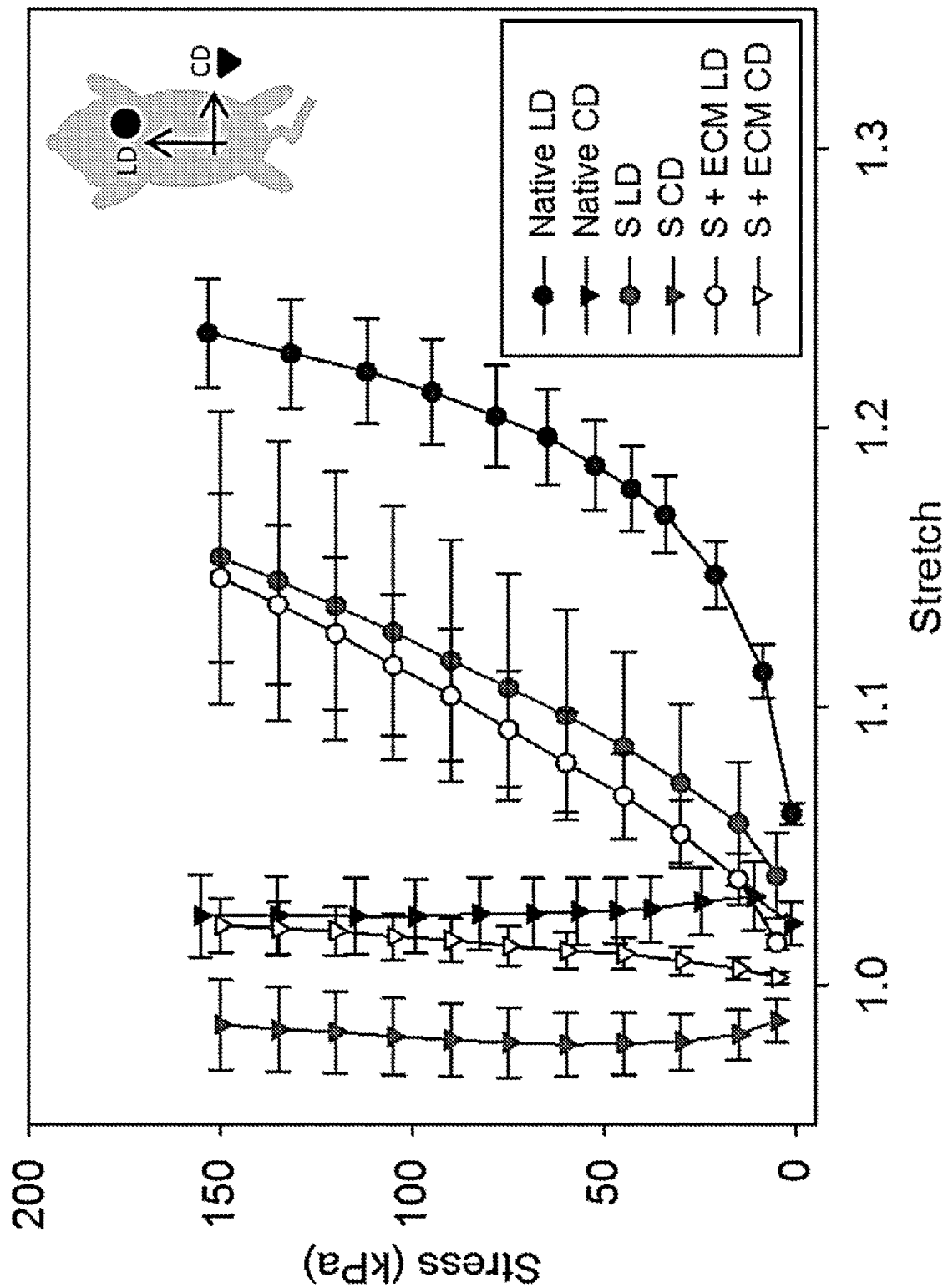
FIGS. 3A-3B. Pre-implantation scaffold mechanics, and release profile.

Pre-implant patch mechanics were characterized with biaxial testing (n≥5/group) to verify the efficacy of the scaffold fabrication method to induce anisotropy and stiffness comparable to native tissue (FIG. 3A). Square samples 10×10 mm in size were tested under stress control following a methodology described by Sacks Biaxial Mechanical Evaluation of Planar Biological Materials. Journal of elasticity and the physical science of solids 61, 199, 2000, 150 kPa was estimated as the stress value corresponding to a range of stretch values (1.0-1.20) induced by breathing on the rat abdomen under physiological conditions. Sample thickness was measured with a dial micrometer (L.S. Starrett Co.,Athol, Mass., USA). Fiducial markers were affixed at the four corners of a 5×5 mm center area within the samples, a deformation gradient tensor was then calculated based on the position of the markers and displacement field derived from shape functions. Tests were initiated with preconditioning followed by 10 cycles of testing (30 s each) at room temperature in PBS. A free-floating configuration was utilized for the reference system in post-processing. The ultimate tensile properties of scaffolds in the wet state were evaluated by uniaxial tensile testing employing an MTS Insight (MTS, Eden Prairie, Minn.) with a 10 N (0.01 N resolution) load cell at room temperature. The samples were extensionally deformed at 10 mm/min according to ASTM D638M. Young's modulus was calculated based on the initial slope of the stress vs. strain curve ($0 \leq \varepsilon \leq 10\%$) using linear regression. The ultimate stress was determined as the maximum stress.

Histology

Figure 4G:
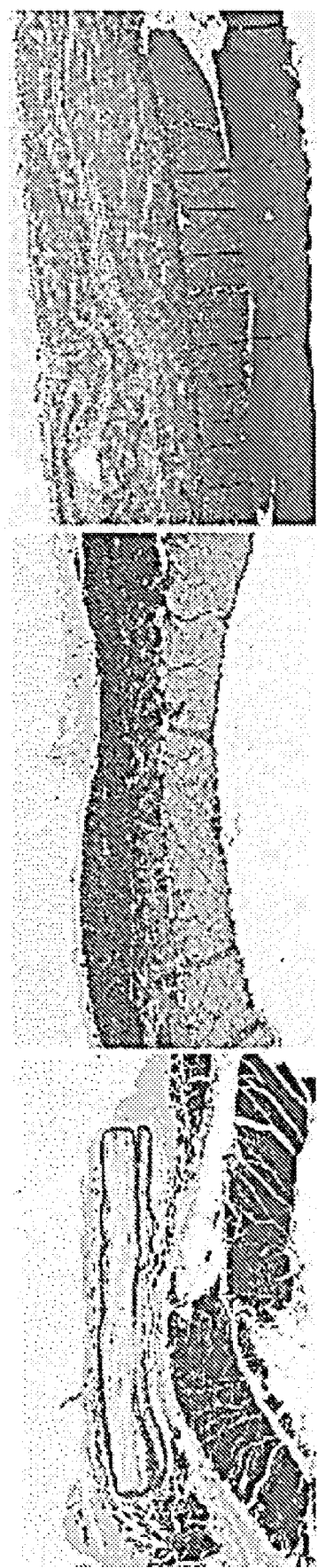
Figure 4H:
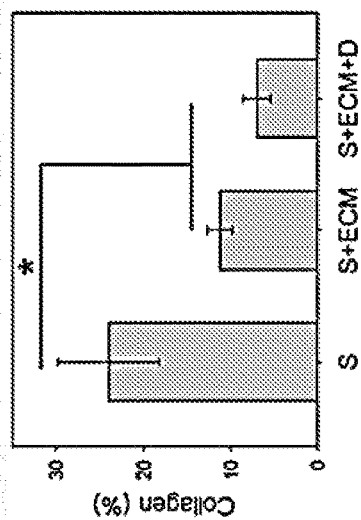

At 8 wk post-implantation samples were retrieved, fixed in 10% formalin solution for ≥24 h, embedded in paraffin and serially sectioned into specimens 10 μm in thickness. Next, hematoxylin and eosin (H&E) and Masson' trichrome (MT) staining of pre implantation scaffolds and explants were utilized to evaluate: polymeric fiber volume, newly formed tissue, cellular infiltration, and scar area (FIG. 4-FIG. 5). In order to assess the foreign body response a custom-made algorithm, developed in Matlab (Mathwork, Natick Mass.), was utilized to segment and quantify collagen rich areas (FIG. 4G-4H). The algorithm is based on a two-phase iterative process known as k means clustering. In step one, given an integer k and an array of data, k cluster centroids were identified minimizing the total squared Euclidean distance between each pixel and its closest RGB centroid. With k=4, the algorithm segmented each image into 4 color groups corresponding to background, muscle tissue, collagen or de-novo ECM, and scaffold. In step two, collagen pixels were identified as those pixels which had a blue/red pixel intensity ratio of approximately 2: red<125, blue>210.

At the macroscopic scale, cross sections were utilized to quantify explant thickness. NIH Image J was utilized to identify the explant central line, draw equi-spaced segments (n=10) perpendicular to this line intersecting the abdominal wall border, and calculate the mean of their lengths. This measure was coupled with in situ explant visual inspection (FIG. 6).

Animal and Surgical Models

The animal study was performed following US National Institutes of Health guidelines for animal care, and was approved by the Institutional Animal Care and Use Committee of the University of Pittsburgh. The experiment was performed in compliance with both the Animal Welfare Act Regulations and Federal statutes relating to animals and experiments involving animals and adhered to the principles defined in the Guide for Care and Use of Laboratory Animals, National Research Council, 1996.

Adult female Sprague-Dawley rats 10-12 wk old, ~250 g in weight (Harlan Sprague Dawley Inc., Indianapolis, Ind., USA) were used for the abdominal wall repair procedure. The experiment was designed to assess the effects of $NO_2$-FA controlled release on angiogenesis. Therefore, a partial wall defect was preferred to a full wall defect model, this enabled evaluation of the impact of drug release on the tissue underneath the abdominal wall patch. The surgical protocol was adapted from a procedure previously established Lai et al. Peritoneal Regeneration Induced by an Acellular Bovine Pericardial Patch in the Repair of Abdominal Wall Defects. Journal of Surgical Research 127, 85, 2005. In brief, inhalation of 1.25-2.5% (maintenance-induction) isoflurane with 100% oxygen was adopted as anesthetic. The skin was shaved and the surgical field was prepared by sterilization with povidone-iodine solution, the rats were positioned in dorsal recumbency on a heating blanket, the operating environment was kept sterile during the procedure. An incision was made 2 cm inferior to the xiphoid process. Next, a square shape partial thickness defect with a side of 1 cm and a depth of ~300 μm was dissected and removed, this included the abdominal wall fascia and part of the muscle, the peritoneum was left intact, while skin and subcutaneous tissue were recomposed at the end of the procedure. All the patches were sutured by three equal-spaced 7-0 polypropylene sutures to minimize the foreign body response elicited by the polypropylene and better assess the impact of the different scaffolds on angiogenesis. Abdominal wall patches were oriented so that the stiffer direction of the material was aligned with the circumferential direction of the rat abdomen, scaffold notches placed for this purpose (straight edge on disc shaped scaffolds) ensured proper alignment. S-ECM and S-ECM-D groups were implanted with the ECM component of the scaffold facing the wall defect; this "open face sandwich" approach was meant to promote a direct interaction of the ECM component with the treated area. Finally, the skin closure was obtained by double-layer buried suture and the animals remained in the surgical suite under observation until recovered from anesthesia. Postoperative care followed the standard protocol. Animals were euthanized by isoflurane (5%) inhalation at 8 wk after the procedure (S group n=6, S+ECM and S+ECM+D n=10 each). The patches were explanted by cutting approximately 5 mm outside of the suture line and retrieved samples were processed for the histological and immunofluorescence assessment.

Blood Vessel Morphological Assessment

Regional angiogenesis was investigated by combining morphological with topological information. Morphological assessment included quantification of blood vessel/$mm^2$ and vessel type and was performed with two distinct experiments: histological (FIG. 7, 9) and immunofluorescence assessment (FIG. 8).

For the histology, MT stained cross sections (n≥5 animals/group) were pre-processed as discussed in section 2.7. Explant cross sections examined with immunofluorescence (n≥5 animals/group) were pre-processed with fixation on 4% phosphate buffered paraformaldehyde solution (4 hr), followed by immersion in 30% sucrose solution (>48 hr), embedding into OCT compound (Tissue-Tek, Torrance, Calif.) and finally sectioned with a 10 µm step size. Next, sections were blocked with 10% goat serum in 0.2% Triton—1 X PBS solution (2 hr at room temperature) and treated as in (11) with mouse primary antibody against CD31 (ab64543, 1:100, Abcam) and rabbit primary antibody against αSMA (Ab5694, 1:100, Abcam). Anti-rabbit Alexa Fluor® 594 (A21207; 1/1000, Thermo Fisher Scientific) and biotin-streptadivin Alexa Fluor® 488 (BA-2001, 1:200, Thermo Fisher Scientific-532354, 1:150, Invitrogen) were utilized as secondary antibodies. DAPI mounting medium was utilized to provide nuclear staining, (5 µL/section, DAPI H-1200, Vectashield) while negative controls were obtained from sections only processed with secondary antibody.

A Nikon Eclipse 6600 microscope (Nikon Corporation) equipped with spectral unmixing of autofluorescence system Nuance 3.0.2 (Caliper Life Science Inc.) was utilized to acquire epifluorescent images and to decouple signal of interest from autofluorescence generated by muscle tissue and scaffold. Each MT and CD31/αSMA slide was systematically imaged at 200×(FIG. 9A) covering an extensive region including the area occupied by the abdominal wall patch (inside: I1, I2, I3), the region underneath (below: B1, B2, B3) and the region in proximity to the edges where the material was sutured to the native tissue (left and right: L, R).

Blood vessel number and type were then identified and categorized in different groups with an algorithm utilizing five morphological criteria: (I) diameter size (spanning from 3.7 µm for capillaries to 76 µm for veins), (II) presence of functionally heterogeneous layers (e.g. tunica intima, media and adventitia), (III) layer thickness ratios (e.g. predominant tunica media/comparable intima and media), (IV) shape (e.g. rounded/amorphous), (V) cell type in proximity of the object of interest. The method, previously utilized in (11) allowed for the segmentation of the identified vessels into four major categories a) arterioles and post-capillary veins, b) small arteries and venules, c) small veins, d) arteries and veins. Vessel diameter was measured based on the diameter size of circular cross sections or based on longitudinal vessel sections. Each detected longitudinal cut of the vessel was considered as one count, the diameter was then measured as the distance between the two edges of the vessel.

Blood Vessel Topological Assessment

In order to further investigate the effect of $NO_2$-OA release on regional angiogenesis, the images collected and analyzed as described in the previous section were processed with respect to the explant topology. The total number of vessels detected at different locations of each image were averaged and attributed to the geometrical center of the image on a 3D composite map (combination of 8 images FIGS. 8A-8D) having the volume of the scaffold at its center (white line in FIGS. 9B-9D) and Z values corresponding to the number of vessels detected. Next, these values were further averaged over the different animals within a given group and interpolated using biquintic numerical interpolation (Matlab, MathWorks, Natick, Mass.). Values at the upper edge of the explants, representing the animal skin, were set to zero and utilized as a boundary condition for the numerical interpolation (points U1-U5). The 3D surface obtained was then projected over the XY plane where Z values were represented as colors indicating the number of vessels/$mm^2$. Finally, additional detail was provided by associating vessel types and their spatial distribution (FIGS. 9E-9G). This post-processing strategy allowed for the visualization of color maps describing not only the vessel number, but also their location with respect to the different topological regions. Most importantly, it allowed the identification of different angiogenesis patterns based on the scaffold type.

Macrophage Infiltration

In order to assess macrophage infiltration and polarization (FIG. 10), sections were immunolabeled with the pan-macrophage rabbit primary antibody to CD68 (ab125212; 1:100, Abcam) which was coupled with goat anti-rabbit secondary antibody Alexa Fluor® 488 (A-1108; 1:1500, Thermo Fisher Scientific). The same sections were also processed with the mouse primary antibody to CD163 (sc-58965; 1:100, Santa Cruz), a macrophage phenotype marker commonly associated with the pro-remodeling (M2-like) phenotype. The secondary anti-mouse antibody was Alexa Fluor® 459 labeled (A-11032; 1/200, Invitrogen). Imaging modality and sample selection was the same utilized for the CD31/αSMA co-staining CD163 +and CD68+ positive pixels were identified, their ratio was calculated (FIG. 10E-10F) with a custom-made script developed in Matlab based on Otsu's binary segmentation algorithm.

Statistical Analyses

Statistical analyses were conducted using Sigma plot (Systat Software Inc., Chicago, Ill., USA). One-way analysis of variance (ANOVA) followed by Tukey-Kramer multiple comparison testing was adopted for comparison of multiple samples. In order to compare the biaxial response of the different groups, one-way ANOVA was applied to compare the maximum stretch at 150 kPa stress level for each sample. Results are presented as mean ± standard error of the mean. Differences were considered to be statistically significant when $p<0.05$.

Results

Controlled Release In Vitro Characterization

The ability to control particle size by changing the agitator speed or by utilizing sonication during the double emulsion processing was qualitatively verified via SEM (FIG. 1A-1C), results were corroborated by diameter quantification that showed larger micro-particles being produced at 1000 RPM (FIG. 1E). This yielded different surface/volume ratios which, given the same PLGA chemistry and $NO_2$-OA quantity for the three groups of particles, produced significantly different release profiles (FIG. 1D).

The microparticles fabricated at 1000 RPM had the smallest surface/volume ratio and as such were characterized by the slowest release profile. One intention of the scaffold design endpoints was to extend the in vivo drug release, therefore based on this in vitro characterization, the 1000 RPM-induced microparticles were incorporated in the polymeric matrix and utilized for the rest of the study.

Pre-Implantation Scaffold Structure, Mechanics, and Release Profile

Scaffold visual and histological comparisons are provided in FIGS. 2A-2F. MT stained sections highlighted the single polymer layer structure in the S group, the presence of distinct polymer rich and ECM rich layers for the S+ECM and S+ECM+D groups, and the successful integration of micro-particles within the ECM rich component of the S+ECM+D group. The latter was further verified with multi-photon microscopy, with a representative image stack provided in FIGS. 2G-2J. The microparticle signal acquired by the 595 nm channel (FIG. 2H) enabled the quantification (n=5) of the number of particles/volume of scaffold and the corresponding pmol of $NO_2$-OA (FIG. 11, Table 1). Given an estimated scaffold pre-implantation volume of 39.3 $mm^3$ and a concentration of particles equal to 260/$mm^3$~10,000 micro particles were included. Scaffold biaxial characterization (FIG. 3A) showed the effects of mandrel velocity, microparticles and ECM incorporation on patch anisotropy. Moreover, comparison with native abdominal wall mechanics showed the capacity to recapitulate a physiologically relevant level of anisotropy. The controlled release profile for the S+ECM+D group in lipase solution at 37° C. shown in FIG. 3B completed the pre-implantation sample characterization.

Histological Assessment

Histological assessment of 8 wk explants performed with H&E and MT staining showed reduced fibrous encapsulation and higher cellular infiltration (FIG. 4-5, FIG. 10D) for the S+ECM and S+ECM+D groups when compared to the S group. Significant thickness differences were detected (FIG. 6) showing beneficial and incremental effects of ECM incorporation and of $NO_2$-OA release respectively. Results of immunolabeling with pan-macrophage marker CD68 and M2 specific marker CD163 are shown in FIG. 10.

Blood Vessel Morphological Assessment

MT staining of 8 week cross sections were utilized to quantify blood vessel number/$mm^2$ and type. Representative images in FIG. 7A-7C and FIG. 7D-7F provided examples of vessel formation in proximity to the suture region and underneath the implanted scaffold respectively. Results of the related quantitative analysis are provided in FIG. 7G showing a significantly higher number of vessels/$mm^2$ for the S+ECM group when compared to the S group and an even stronger angiogenic effect associated with the loading of $NO_2$-OA microparticles. In order to further verify this finding, immunofluorescence staining and image analysis was performed. Qualitative observation (FIG. 8A-8D) and quantitative measurement (FIG. 8E-G) showed an increase in vessels/$mm^2$ for the S+ECM+D group. Both MT and immunofluorescence evaluation offered an additional level of detail by providing vessel type quantification (FIG. 7G , FIG. 9D).

Blood Vessel Topological Assessment

Blood vessel topological distribution showed a lack of neo-vessel formation for the S group on regions inside and below the scaffold (FIG. 9B, regions I and B) and weak vessel growth at the edges (FIG. 9B, regions L-R). In contrast, the presence of ECM was associated with blood vessel formation at the core, below and at the edges of the abdominal wall patch (FIG. 9C). $NO_2$-OA release in the S+ECM+D group further emphasized this effect with the highest level of vessels/$mm^2$ at the edges (FIG. 9D, regions L-R). Data were also organized to couple the topological and morphological information, and showed a significantly greater number of capillaries (FIG. 9E) in the S+ECM+D scaffolds regardless of the region. Small arteries, veins, and venules were more numerous in the I1-I3 regions for the S+ECM and S+ECM+D groups when compared to the S group (FIG. 9F). Finally, the number of larger and more mature vessels/$mm^2$ such as arteries and veins was significantly greater in the S+ECM+D, B1-B3 and I1-I3 regions (FIG. 9G). Distinct patterns of angiogenesis (FIG. 9) were consistent with the cellular infiltration and fibrotic response illustrated by the histological analysis.

Discussion

Controlled Release In Vitro Characterization

The degradation profile and the release mechanisms of polymeric micro/nano particles can be modified by a number of factors including: polymer molecular weight (e.g. for PLGA 14k-213k Da), copolymer composition (e.g. for PLGA 85:15, 65:35, 50:50), morphology (e.g. surface topography, nano-channels), or diameter size. In vitro results (FIG. 1) showed the capacity to control the release kinetic of $NO_2$-OA (1mM) up to 7 days by changing the particle size in the 1-50 μm range (FIG. 1D). Release profiles were sigmoidal with larger microparticles inducing a slower release.

Figure 3B:
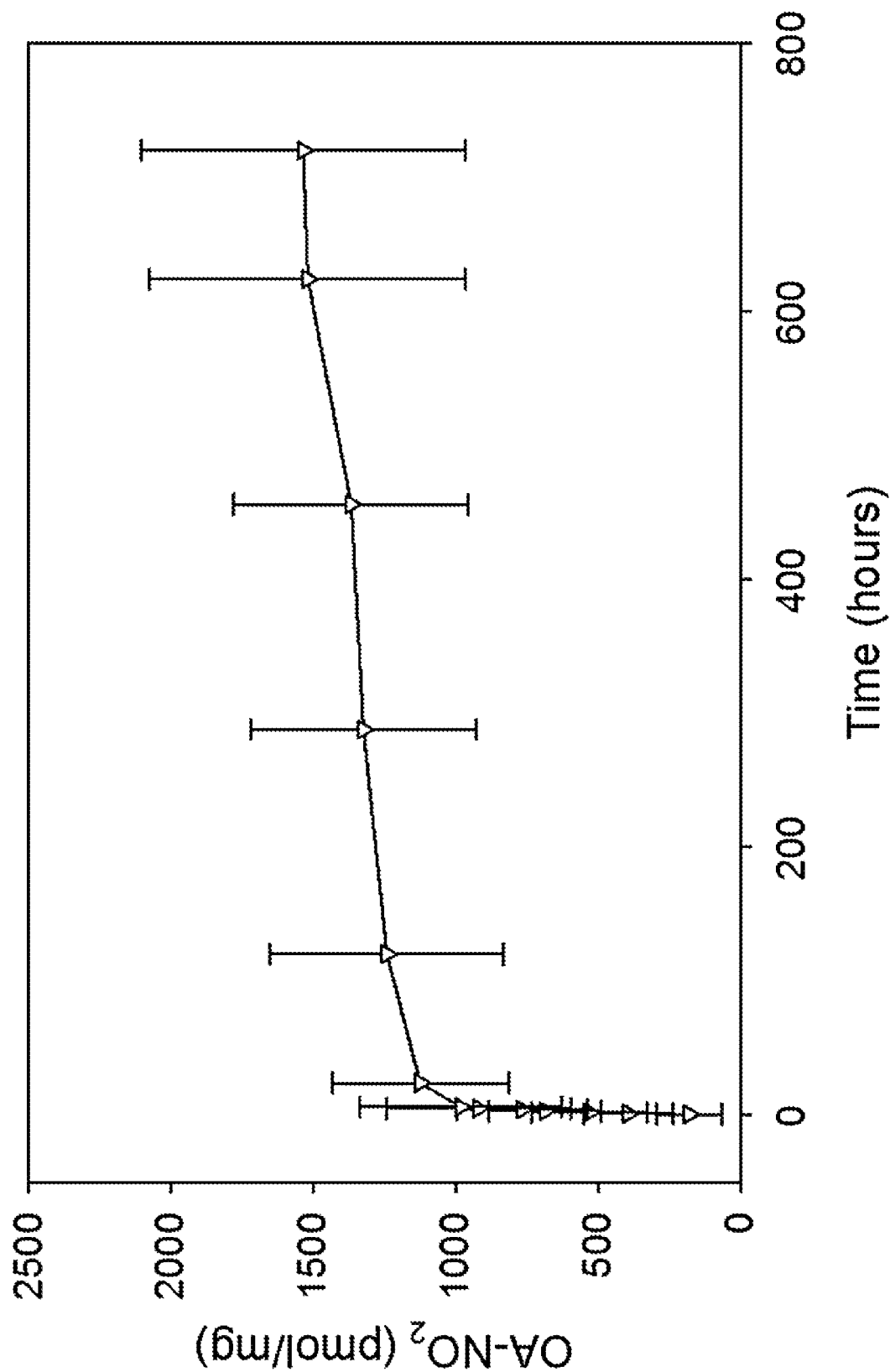

Controlled release from non-woven nanofibrous biodegradable scaffolds was previously demonstrated in where antibiotic drug was combined with electrospun PLGA fibers for the prevention of post-surgical adhesions and infections. Whether drug is loaded into the polymeric fibers or into carried microparticles, the host interacts directly with the release vehicle impacting directly on its degradation. Aiming to extend the rat abdominal wall exposure to $NO_2$-OA, the expected half-lives of PLGA particles were prolonged by the incorporation of the particles into the polymer matrix and/or ECM gel. In order to simulate in vitro a more realistic mechanism, degradation conditions in a static PBS solution were replaced by rocking the samples in a porcine lipase solution at 37° C. (FIG. 3B).

Pre-Implantation Scaffold Structure, Release Profile, and Mechanics

While gross appearance and surgical handling of the abdominal wall patches remained consistent across groups (FIGS. 2A, 2C, 2E), differences in structure were highlighted with MT staining of cross-sections. S-ECM and S-ECM-D groups showed an open-phase bi-layered structure with a clear distinction (FIGS. 2B, 2D, 2F) between the polymer-rich and the ECM-rich regions. In contrast, group S had a simpler, single layer porous structure.

Microparticle inclusion and spatial distribution was confirmed via histological analysis of scaffold cross sections (FIGS. 2B, 2D, 2F) and with three-dimensional detail via multi-photon microscopy (FIGS. G-J). The latter enabled the quantification of the number of particles per unit volume and the pmol $NO_2$-OA/mg of scaffold. Prospectively, this technique can be crucial to estimate the total amount of drug/ scaffold and to investigate the therapeutic dose of the compound to be released. The in vitro release profile of the implanted S-ECM-D group (PLGA loaded with 1 M $NO_2$- OA) remained sigmoidal (FIG. 3B) for up to one month under accelerated degradation conditions.

The effects of mandrel velocity, microparticle integration and ECM inclusion on biaxial mechanics shown in FIG. 3A, were in agreement with previous studies, and demonstrated the capacity to recapitulate physiologically relevant values of anisotropy for the rat abdominal wall (e.g. an equistress 150 kPa produces $\lambda_{PD}$=1.0–1.05, $\lambda_{XD}$=1.2–1.25). Similarly, for the PECUU polymeric material, the Young's modulus, ultimate stress, $T_g$, $T_m$ for PECUU were consistent with values reported in Hong et. al.

Histologic Assessment

There were profound differences between groups in terms of cellular infiltration, scaffold degradation, fibrotic response, (FIGS. 4-5) and abdominal wall thickness (FIG. 6). As for comparative evaluations of electrospun polyurethane and biohybrid (polyurethane+ECM) scaffolds, the S group was less infiltrated by host-recruited cells, the scaffold volume was less degraded and a stronger encapsulating tissue response was observed (FIGS. 4G-4H), in contrast to the histological observations with the S+ECM and S+ECM+D groups. Comparison of xenogeneic porcine small intestinal submucosa (SIS) vs. polypropylene mesh (PPM) for the repair of abdominal wall defects in a large animal model showed major benefits of biologic material derived patches when compared to woven synthetic surgical meshes. In particular, SIS showed better tissue in-growth and fewer adhesions than the PPM. Since then, more than two decades of research has confirmed the better outcomes of SIS materials. For example, assessed tensile strength, collagen formation, and angiogenesis in a rat hernia model repaired with Surgisis® (porcine SIS derived graft), AlloDerm® (acellular human tissue skin derived graft), or Vicryl Woven Mesh® (absorbable synthetic, non-antigenic mesh). Consistent with the histological findings of our current study when an ECM component was included (FIG. 4-5), Surgisis® and AlloDerm® both showed better collagen deposition, enhanced tissue remodeling and cellular in-growth.

In spite of the positive outcomes associated with biologically-derived scaffolds, there are reports of complications with this class of material. Human acellular dermal matrix induced severe inflammation in an adult vervet monkey model. Similarly, a clinical case of rejection for Permacol®, a porcine dermis collagen mesh, has been reported. Perioperative and long-term outcomes of porcine dermal matrix for human abdominal wall repair have been reported to have a 42% post-surgery complication rate, which included a 27% incidence of hernia recurrence. These reports have stimulated interest in alternative solutions such as the biohybrid approach presented in the present study.

Improved host cell infiltration and reduced material encapsulation, noted histologically (FIGS. 4-5, FIG. 10D), was also corroborated at the macroscopic level by wall thickness measurements of explants at 8 wk, where the S+ECM+D group showed the closest value to the healthy native abdominal wall (FIG. 6). The histologic evidence cumulatively suggested beneficial effects of controlled, regional $NO_2$-OA release. Wall thickness measurements were also comparable with previous studies (range: 0.8-1.6 mm) utilizing elastomeric polyurethane fibrous scaffolds, including those incorporating muscle-derived stem cells, in the same animal model and at the 8 wk time-point.

Blood Vessel Morphological Assessment

Neovascularization is widely recognized (8, 46-48, 52-53) as a key metric reflecting both positive and adverse outcomes of biomaterials and engineered constructs for abdominal wall repair. Yet, blood vessel morphology, type and spatial distribution remain generally unaddressed. Most commonly, qualitative evaluation of von Willebrand factor (vWf) or CD31 immunostaining, MT, and H&E histological sections (48, 52-53) are employed to quantify the number of vessels on randomly selected high-magnification images (e.g. n=4 at 40×(46-47), n=7-10 at 100×(8, 51)) without performing vessel segmentation based on morphology and spatial distribution.

The current study provided increased quantitative insight into angiogenesis by evaluating two independent indices: MT staining and immunofluorescence via CD31 and αSMA co-localization. According to both methodologies (FIGS. 7, 8), the S+ECM+D group reported greater angiogenesis at 8 wk compared to the other groups. Although cellular infiltration was greater when ECM was present in the scaffolds, macrophage infiltration (FIG. 10) did not show significant differences between the groups. Comparison between the S and S+ECM groups in FIG. 7 shows a significant effect of the ECM integration on the number of vessels/mm². An additional effect is then produced by the controlled release of $NO_2$-OA as shown by the comparison of the S+ECM+D vs. the S and S+ECM groups in FIGS. 7-8. Blood vessels were also segmented within three different categories: I) capillaries, II) small arteries, veins and venules, and III) arteries and veins (FIG. 7, 8) based on a multi-criteria algorithm. The total number of identified vessels/mm² was in agreement with previous, less specific quantification (30-40/mm²) performed on comparable biomaterials and animal model.

Blood Vessel Topological Assessment

The additional detail provided by the assessment described in the previous section was complemented with topological mapping of neovessels (FIG. 9). While section location had a profound effect on outcomes of histologic evaluation, many analyses have not addressed this factor, imaging random areas in the region of interest. Averaging over a spatial region of interest might lead to the loss of relevant information. For instance, areas occupied by surgical sutures or at the tissue-biomaterial interface are characterized by a more robust inflammatory response at early time points. The bulk of the scaffold volume is less likely to be infiltrated with cells than the periphery. Drug release will also be spatially dependent and can differentially affect the tissue directly underneath the scaffold more than distal tissue sections.

The present study overcomes these limitations by systematically mapping angiogenesis inside and around the abdominal patch volume. Groups differed in terms of the bulk number of vessels and also revealed distinct vascular growth patterns (FIG. 9 B-D). The S group, consistent with the rest of the histological evaluation (FIGS. 4-5), was mostly engulfed into a collagen capsule and showed only limited vessel growth at the patch edges (FIGS. 8B, E-G, regions L and R). In contrast, the ECM component within the S+ECM group was associated with cell infiltration and vessel growth at the core of the scaffold, where small arteries, veins and venules, as well as arteries and veins were more frequently observed compared to the S group (FIG. 9C, E-G region I). The impact of local differences in $NO_2$-OA concentrations in the S+ECM+D group (FIG. 9D) was significant for capillaries in three regions: below (B), inside (I) and at the edges (L and R) (FIG. 9E). Significant differences were also measured for the small arteries, veins and venules (FIG. 9F), with the region inside the scaffold with the S+ECM+D exhibiting more vessels then the S group. This was also the case for the arteries and veins category in regions (FIG. 9G) below and inside the scaffold. As expected, capillaries were the most abundant, regardless of the group, followed by small arteries, veins and venules and finally by larger arteries and veins.

Abdominal Wall Repair and Enhanced Angiogenesis: Technology Overview

Alternatives to autologus tissue for abdominal wall repair include a vast spectrum of biomaterials and tissue engineering approaches. Early attempts focused on improving performance and resistance to adhesion of non degradable woven surgical meshes, yet the increasing clinical success of biologic scaffolds gave impetus to a shift towards the development of ECM-based meshes such as decellularized xenogenic dermis or SIS, decellularized allogeneic tissue, decellularized and then cell-seeded xenogeneic tissue and decellularized bovine pericardium. This class of biomaterials has generally achieved favorable endpoints in terms of in situ remodeling with cases showing long term evidence of new skeletal muscle fiber formation and innervation.

In spite of these achievements, witnessed by the large number of biological surgical meshes now being used clinically, post-surgical hernia recurrence remains problematic, and control over the structure and function of abdominal wall support devices is still limited. This motivates the introduction of alternative paradigms capable of balancing the higher level of processing control associated with synthetic materials and the superior bioactivity of ECM-derived meshes. Experience with biodegradable woven meshes, as opposed to devices designed to remain permanently in the host, can reduce the risk of chronic inflammation while mitigating mechanical mismatch at the tissue-device interface. Incorporation of an ECM component, such as including cell seeded synthetic—biologic composite woven constructs or biohybrid and biodegradable non-woven scaffolds, may also provide improved biological response and less risk for chronic morbidity. While adverse effects in terms of immune response to the scaffold implantation can be equally induced by a biological as well as by a biohybrid material, the adoption of ECM scaffolds (not integrated with a polymeric matrix) limits control of patch morphology and mechanics. Key biomaterial features such as: pore size, pore interconnectivity, elastic modulus, tissue anisotropy, depend on the tissue source and are fundamentally affected by the decellularization process. A recognized advantage of the bio-hybrid therefore consists on the ability to combine biological material bioactivity with the higher control of the structure—function typically provided by synthetic material processing methods. Regional angiogenesis is often noted as a critical factor related to positive clinical outcomes. However, virtually no biomaterials and tissue constructs specifically focus on approaches that facilitate and sustain neovascularization.

Activity of NO2-OA in Abdominal Wall Repair $NO_2$-OA, as a thiol-reactive electrophilic fatty acid, will be by nature a pleiotropic signaling mediator. The unique nature of nitroalkene substituents promotes both kinetically rapid and reversible Michael addition reaction. Current data support that these post-translational protein modification reactions, including those with adaptive signaling mediators such as Keap1/Nrf2, sEH, PPARγ and NF-κB p65 subunit, are non-toxic and induce anti-inflammatory responses. The preclinical actions of $NO_2$-OA have been reported in murine models of vascular restenosis, cardiac ischemia-reperfusion injury, atherosclerosis, and diabetes among others. A recent study showed that $NO_2$-OA decreases myocardial fibrosis and modulates functional polarization of M1 and M2 macrophage sub-populations. These results are consistent with the present abdominal wall repair and macrophage infiltration responses. While there were no statistically significant differences between pro-inflammatory (M1-like) and pro-remodeling (M2-like) macrophage phenotypes, this might be explained by the fact that healthy native abdominal wall conditions were being re-established. Finally, $NO_2$-OA activates Nrf2—dependent gene expression, which in turn regulates pro-angiogenic mediator and HIF-1α gene expression, stimulating capillary-like sprouts ex vivo and angiogenesis in chicken egg membranes. The present data reveal that $NO_2$-OA promotes neovascularization in the rat abdominal wall by increasing the number of capillaries, small arteries, veins, and venules.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for repairing at least a portion of an abdominal wall of a subject, comprising applying a construct to the portion of the abdominal wall, wherein the construct comprises:
    a dermal extracellular matrix gel;
    polymer fibers; and
    microparticles comprising 10-nitro-9-trans-octadecenoic acid encapsulated by poly(lactic-co-glycolic acid), wherein the microparticles have an average diameter of 40 to 50 µm, and release of the 10-nitro-9-trans-octadecenoic acid enhances neovascularization at the portion of the abdominal wall.

2. The method of claim 1, wherein the polymer fibers comprise a poly(ester carbonate)urethane urea.

3. The method of claim 1, comprising a bi-layer scaffold of the dermal extracellular matrix gel and the polymer fibers, wherein the microparticles are included within the bi-layer scaffold.

4. The method of claim 1, wherein the polymer fibers comprise poly(ester urethane) urea (PEUU), poly(ether ester) urethane urea (PEEUU), or poly(carbonate) urethane urea (PCUU).

5. The method of claim 1, comprising a bi-layer scaffold of the dermal extracellular matrix gel and the polymer fibers, wherein a first layer is extracellular matrix gel-rich and a second layer is polymer fiber-rich.

6. The method of claim 1, wherein release of the 10-nitro-9-trans-octadecenoic acid increases abdominal wall thickness.

7. A method for repairing at least a portion of an abdominal wall of a subject, comprising applying a construct to the portion of the abdominal wall, wherein the construct comprises:
    a hydrogel, wherein the hydrogel is carboxymethylcellulose, polyacrylic acid, agar, arabic gum, alginate, alginic acid, gelatin, starch, methylcellulose, hydroxyethylcellulose, tragacanth gum, or a mixture thereof;
    polymer fibers; and
    microparticles containing a nitro oleic acid agent comprising 10-nitro-9-trans- octadecenoic acid encapsulated by poly(lactic-co-glycolic acid), wherein the microparticles have an average diameter of 40 to 50 µm, and release of the 10-nitro-9-trans -octadecenoic acid agent enhances neovascularization at the portion of the abdominal wall.

8. The method of claim 7, wherein release of the 10-nitro-9-trans-octadecenoic acid increases abdominal wall thickness.

9. The method of claim 7, wherein the polymer fibers comprise a poly(ester carbonate)urethane urea.

* * * * *